US012415085B2

(12) United States Patent
Frangineas, Jr. et al.

(10) Patent No.: US 12,415,085 B2
(45) Date of Patent: Sep. 16, 2025

(54) PHASE ADJUSTED COIL EXCITATION FOR MUSCLE STIMULATION

(71) Applicant: ZELTIQ Aesthetics, Inc., Pleasanton, CA (US)

(72) Inventors: George Frangineas, Jr., Fremont, CA (US); Like Zeng, Pleasanton, CA (US); Joel N. Jimenez Lozano, Pleasanton, CA (US)

(73) Assignee: Zeltiq Aesthetics, Inc., North Chicago, IL (US)

( * ) Notice: Subject to any disclaimer, the term of this patent is extended or adjusted under 35 U.S.C. 154(b) by 850 days.

(21) Appl. No.: 17/530,447

(22) Filed: Nov. 18, 2021

(65) Prior Publication Data

US 2022/0152409 A1    May 19, 2022

Related U.S. Application Data

(60) Provisional application No. 63/116,140, filed on Nov. 19, 2020.

(51) Int. Cl.
*A61N 2/00*    (2006.01)
*A61N 2/02*    (2006.01)

(52) U.S. Cl.
CPC ............. *A61N 2/004* (2013.01); *A61N 2/02* (2013.01)

(58) Field of Classification Search
CPC .......... A61N 2/00; A61N 2/002; A61N 2/004; A61N 2/006; A61N 2/008; A61N 2/02
See application file for complete search history.

(56) References Cited

U.S. PATENT DOCUMENTS

| | | |
|---|---|---|
| 10,471,269 B1 | 11/2019 | Schwarz et al. |
| 10,478,634 B2 | 11/2019 | Schwarz et al. |
| 10,493,293 B2 | 12/2019 | Schwarz et al. |
| 10,556,122 B1 | 2/2020 | Schwarz et al. |
| 10,632,321 B2 | 4/2020 | Schwarz et al. |
| 10,688,310 B2 | 6/2020 | Schwarz et al. |
| 10,695,575 B1 | 6/2020 | Schwarz et al. |
| 10,695,576 B2 | 6/2020 | Schwarz et al. |
| 10,709,894 B2 | 7/2020 | Schwarz et al. |

(Continued)

FOREIGN PATENT DOCUMENTS

| | | |
|---|---|---|
| DE | 202016008804 U1 | 10/2019 |
| JP | 2015107176 A | 6/2015 |

(Continued)

*Primary Examiner* — Carrie R Dorna

(57) ABSTRACT

Systems and methods can be implemented in which an electromagnetic charge is used to strengthen, tone, and firm muscle tissues. For example, the method may include receiving parameters for operation of a magnetic muscle stimulation device. The method may also include causing, based on the received parameters, a first alternating current having a first phase to flow through a first coil and generate a first time-varying magnetic field that induces a first electric charge in muscle tissue under a skin surface of a patient when the first applicator surface is positioned substantially on and parallel to the skin surface of the patient. The method may also include causing a second alternating current having a second phase to flow through a second coil in a similar manner. Optionally, a phase offset between the first and second phases may be adjusted to limit to a predetermined maximum electric charge.

28 Claims, 16 Drawing Sheets

(56) References Cited

U.S. PATENT DOCUMENTS

| | | | |
|---|---|---|---|
| 10,709,895 B2 | 7/2020 | Schwarz et al. | |
| 11,266,852 B2 | 3/2022 | Schwarz et al. | |
| 11,464,994 B2 | 10/2022 | Schwarz et al. | |
| 11,497,925 B2 | 11/2022 | Schwarz et al. | |
| 11,590,356 B2 | 2/2023 | Schwarz et al. | |
| 11,691,024 B2 | 7/2023 | Schwarz et al. | |
| 11,794,029 B2 | 10/2023 | Schwarz et al. | |
| 2015/0157873 A1 | 6/2015 | Sokolowski | |
| 2016/0151637 A1 | 6/2016 | Abe et al. | |
| 2018/0001107 A1 | 1/2018 | Schwarz et al. | |
| 2019/0201706 A1 | 7/2019 | Schwarz et al. | |

FOREIGN PATENT DOCUMENTS

| | | | | |
|---|---|---|---|---|
| JP | 2015521879 A | | 8/2015 | |
| WO | WO2018136431 | * | 7/2018 | ............ A61N 2/006 |
| WO | WO-2018136431 A1 | * | 7/2018 | ............ A61N 2/006 |

* cited by examiner

ENERGY DELIVERY VALUE 290

Satisfy at least one of:
1. Tissue-Independent Integrated Electric Charge / Electrical Conductivity >= 0.115 millivolt second meters (mV * s * m)
2. Maximum Magnetic Flux Density = 1.3 to 1.4 teslas (T)
3. Maximum Current Density Norm >= 40 amps / square meter (A/m²)
4. Induced Current Peak-to-Peak >= 70 milliamps (mA)

PARAMETER RANGE 292

Satisfy each of:
1. Pulse amplitude = Approx. 1500-2500 A
2. Pulse duration / width = Approx. 300-450 microseconds (μS) (2.2 to 3.3 KHz)
3. Waveform frequency = 30 or more pulses per second (pps, or Hz for waveform)
4. Duty Cycle >= 35%
To Result in a pulse charge (Integrated Electric Charge) >= 6.4 μC

PARAMETER SET 294

Set pulse parameter values to:
1. Pulse amplitude = 2000 A
2. Pulse duration = 360 μS (approx. 2.8KHz)
3. Waveformfraquency = 40 Hz
4. Dutycycle = 50%
To Result in a pulse charge of approx. 8 μC

FIG. 2A

Dual Applicators, Geometric Model, In-Phase AC Excitation

PHASE ADJUSTED COIL EXCITATION FOR MUSCLE STIMULATION

CROSS REFERENCE TO RELATED APPLICATIONS

This application claims the benefit of U.S. Provisional Application No. 63/116,140, filed Nov. 19, 2020, entitled "Phase Adjusted Coil Excitation for Muscle Stimulation," which is hereby incorporated by reference in its entirety.

TECHNICAL FIELD

The present disclosure generally relates to muscle stimulation, and more specifically relates to methods and systems for using phase adjusted coil excitation to provide safe and effective muscle stimulation for toning, strengthening, and firming of muscle tissues.

BACKGROUND

Muscle stimulation technologies such as electrical muscle stimulation (EMS) can be helpful for applications such as workout recovery and enhancement, physical therapy, and muscle strengthening and toning. EMS devices may require multiple electrodes to be attached to the skin of the user, which may present a high barrier for regular use. Electrical current is emitted by positive electrodes, passes through skin and other tissue, including muscle, then is returned to the EMS device via negative electrodes. Providing sufficient levels of electrical current with EMS devices to stimulate the muscle tissues often causes nerve endings to be unduly stimulated as well, causing unwanted side effects and discomfort to the user, and limiting the amount of current which can be used.

Other forms of muscle stimulation are also available, such as magnetic muscle stimulation (MMS). These technologies seek to stimulate muscle tissues through electromagnetic fields, avoiding cumbersome skin electrodes and unwanted nerve stimulation which results by bidirectionally passing current through the skin as a means of getting the current to the muscle. However, existing devices are still developing technology and may not currently meet user expectations in regards to, for example, muscle strength, muscle toning, muscle firming, user comfort, safety, the number of therapy sessions required and the length of the treatment period before readily perceivable and tangible results can be realized. Accordingly, there is a need for improved muscle stimulation methods and systems that can deliver highly effective muscle tissue stimulation to remedy these deficiencies.

SUMMARY

According to various implementations, a method for using phase adjusted coil excitation to deliver effective amounts of electromagnetic charge to muscle tissues is provided. The method may include providing a magnetic muscle stimulation device comprising a first device applicator having a first coil positioned in a first housing of the first device applicator, and a second device applicator having a second coil positioned in a second housing of the second device applicator, wherein the first and second housings have a substantially flat applicator surface, and wherein the first and second coils are positioned in the respective housings with an axis of the each coil substantially perpendicular to the each respective applicator surface. The method may also include receiving parameters for operation of the magnetic muscle stimulation device. The method may also include causing, based on the received parameters, a first alternating current having a first phase to flow through the first coil and generate a first time-varying magnetic field that induces a first electric charge in a first portion of muscle tissue under a skin surface of a patient when the first applicator surface is positioned substantially on and parallel to the skin surface of the patient. The method may also include causing, based on the received parameters, a second alternating current having a second phase to flow through the second coil and generate a second time-varying magnetic field that induces a second electric charge in a second portion of the muscle tissue when the second applicator surface is positioned substantially on and parallel to the skin surface of the patient. The method may also include adjusting a phase offset between the first phase of the first alternating current and the second phase of the second alternating current to an offset value that limits a product of the first and second electric charges, in a third portion of the muscle tissue between the first and second portions, to a predetermined maximum electric charge when the first coil and the second coil are within a predetermined distance to each other. In some implementations, the phase offset may be conservatively set to not exceed either 90, 30, 10, 1, or 0 degrees, to ensure some field cancellation between the coils.

Other aspects include corresponding systems, apparatuses, and computer program products for implementation of the computer-implemented method.

Further aspects of the subject technology, features, and advantages, as well as the structure and operation of various aspects of the subject technology are described in detail below with reference to accompanying drawings.

DESCRIPTION OF THE FIGURES

Various objects, features, and advantages of the present disclosure can be more fully appreciated with reference to the following detailed description when considered in connection with the following drawings, in which like reference numerals identify like elements. The following drawings are for the purpose of illustration only and are not intended to be limiting of this disclosure, the scope of which is set forth in the claims that follow.

FIG. 2A depicts example parameters for use with the system of FIG. 1A, according to various aspects of the subject technology.

DESCRIPTION

While aspects of the subject technology are described herein with reference to illustrative examples for particular applications, it should be understood that the subject technology is not limited to those particular applications. Those skilled in the art with access to the teachings provided herein will recognize additional modifications, applications, and aspects within the scope thereof and additional fields in which the subject technology would be of significant utility.

The subject technology provides a magnetic muscle stimulation device with multiple applicators having phase adjusted coil excitation for delivering continuously pulsed electromagnetic current and charge to muscles for strengthening, toning, and firming muscle tissues. Multiple applicators may be utilized to treat a larger muscle volume of a patient at a time, enabling more convenient treatment options by reducing therapy session frequency and duration. However, using multiple applicators may also cause unwanted side effects, such as overstimulation, patient discomfort, and other issues. By adjusting the pulsed waveforms delivered to the coils of the multiple applicators to be in-phase or near in-phase, these unwanted side effects can be minimized to provide effectively targeted muscle stimulation over a wider treatment area. More specifically, when the pulsed waveforms are in-phase, the directions of the induced voltages within overlapping treatment areas tend to oppose each other, resulting in cancellation effects that advantageously reduce the risk of overstimulation.

Figure 1A:
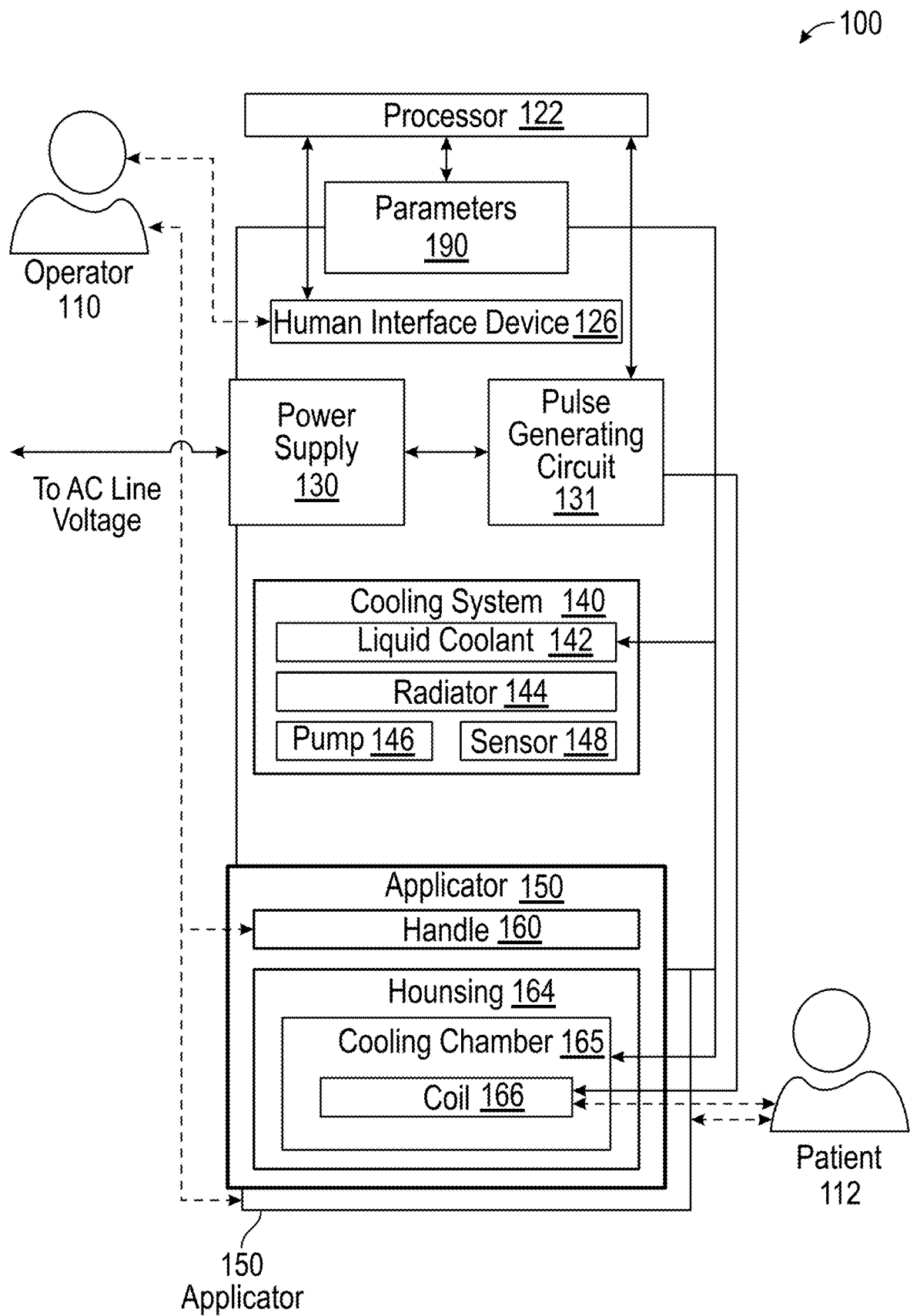
FIG. 1A depicts an example system for using phase adjusted coil excitation to deliver effective amounts of electromagnetic charge to muscle tissues, according to various aspects of the subject technology.

FIG. 1A depicts an example system 100 for using phase adjusted coil excitation to deliver effective amounts of continuously pulsed electromagnetic charge to muscle tissues of patient 112, according to various aspects of the subject technology. Base unit 120 includes processor 122, human interface device 126, power supply 130, pulse generating circuit 131, cooling system 140, and parameters 190. Cooling system 140 includes liquid coolant 142, radiator 144, pump 146, and sensor 148. Applicator 150 includes handle 160 and housing 164. A cover may optionally attach to the outside of housing 164 and/or handle 160.

As shown in FIG. 1A, operator 110 may use human interface device 126 to control base unit 120. Operator 110 may correspond to a healthcare professional, such as a doctor or nurse, that is trained in the usage of system 100. Human interface device 126 includes an input and/or an output device, and may be implemented as, for example, a touchscreen panel, a keypad and a display, or a similar interface device. In one implementation, operator 110 may use human interface device 126 to adjust parameters 190, or to select or define a parameter set that satisfies parameters 190. In other implementations, parameters 190 may be predetermined at manufacture time and may not be changed by operator 110. In this case, parameter sets may also be predefined, or operator 110 may select from one or more predetermined parameter ranges or parameter sets, as shown in greater detail in FIG. 2A.

Base unit 120 may include several other components, as shown in system 100. Base unit 120 may include processor 122, which may correspond to any type of general or specialized processor, controller, integrated circuit, application specific integrated circuit (ASIC), field programmable gate array (FPGA), system-on-chip, or similar device, and may include hardcoded circuit elements, firmware, software, or any combination thereof.

Base unit 120 may include power supply 130, which may be any type of power supply, such as a switching power supply, and may be connected to AC line voltage mains, for example 100V AC to 230V AC. Power supply 130 may provide power to pulse generating circuit 131, which may in turn excite coil 166 based on parameters 190. Power supply 130 may be a separate and independent power supply from a general power supply (not shown) that supplies power to other components of base unit 120, such as processor 122, human interface device 126, and cooling system 140. In some implementations, one or more batteries or other alternative power sources may be provided to provide a graceful shutdown or to continue operation in the event power supply 130 or the general power supply fails.

Base unit 120 may include cooling system 140, which is preferably a high-performance cooling system such as a liquid cooling system. Air cooling may also be used but may be insufficient to meet the operating demands of parameters 190 when optimized for high performance muscle stimulation. As shown in system 100, cooling system 140 is a liquid cooling system that includes liquid coolant 142, radiator 144, pump 146 and sensor 148. Pump 146 may be used to circulate liquid coolant 142, which may be thermally coupled to coil 166 and other heat generating components of system 100. Radiator 144 may be used to regulate the temperature of liquid coolant 142 to keep coil 166 and housing 164 in a safe operating temperature range. For example, one or more fans may be coupled to radiator 144 to disperse heat from liquid coolant 142 into the atmosphere. Alternative implementations may directly couple cooling system 140 to a central heating ventilation and air conditioning (HVAC) system. Sensor 148 may detect the temperature of liquid coolant to allow fans on radiator 144 to be ramped up or down in speed and to provide processor 122 with temperature monitoring.

Figure 1B:
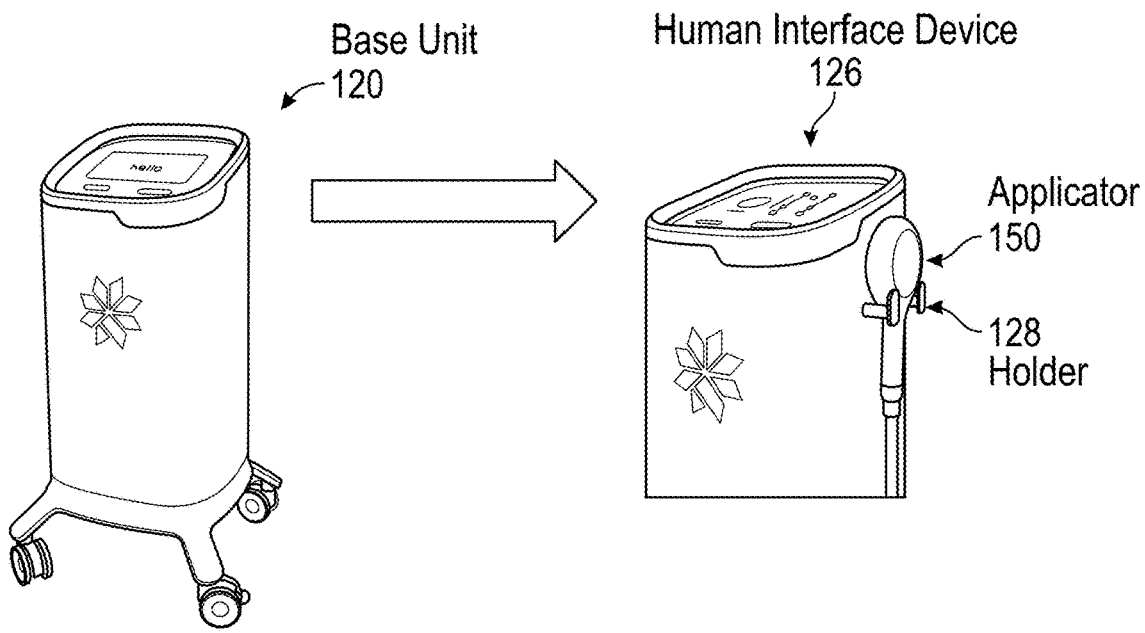
FIG. 1B depicts perspective views of an example base unit for use with the system of FIG. 1A, according to various aspects of the subject technology.

To begin a therapy session, operator 110 may use handle 160 of applicator 150 to position applicator 150 above and substantially parallel to a skin layer of the patient, such that coil 166 stimulates the muscle tissues of patient 112 for toning, strengthening, and firming of the muscle tissues. Multiple applicators may be utilized, such as two of the applicators 150 shown in FIG. 1A. In this regard, processor 122 may direct pulse generating circuit 131 to generate a pulsed waveform to flow into each coil 166 of each applicator 150 (FIG. 1D). To excite coil 166 according to parameters 190, processor 122 may direct pulse generating circuit 131 to generate an alternating current (AC) waveform having a specific parameter set of parameter values, as described in further detail in FIG. 2A. As will be described further below, the pulsed waveform may be substantially in-phase between the multiple coils of the multiple applicators 150. While coil 166 is shown as a single coil, it should be understood that coil 166 may comprise multiple adjacent coils, for example, operating in parallel.

Pulse generating circuit 131 is operably connected to processor 122 and may contain one or more capacitors and one or more switching elements that operate to generate a current through coil 166. Pulse generating circuit 131 may define, together with coil 166, a LC resonant circuit. The switching frequency of the switching elements may be controlled by processor 122 to charge and discharge capacitors in a coordinated manner according to parameters 190, to generate an alternating current through coil 166. The geometry of coil 166 and the pulsed waveform of the current flowing through coil 166 cause the coil to generate a time-varying magnetic field of a desired field strength. The rate of change of the magnetic field induces a corresponding electric current within neuromuscular tissue at a given distance from the coil. As will be described further, processor 122 is configured to, when configured with a set of predefined parameters, drive pulse generating circuit 131 to cause an alternating current to flow through the coil to generate a time-varying magnetic field sufficient to generate an integrated electric charge divided by electrical conductivity, per pulse, equal to or greater than 0.115 millivolt second meters (mV*s*m) in muscle tissue under a skin layer of a patient. It has been found that integrated electric charges/electrical conductivity less than 0.115 mV*s*m under treat patients and create unsatisfactory results. Optimally, the integrated electric charge/electrical conductivity can exceed any of 0.12, 0.13, 0.14, 0.15, 0.16, 0.17, 0.18, 0.19, 0.20, 0.22, 0.25 mV*s*m, and be between 0.12-0.75 mV*s*m. As the charge is increased, patient discomfort can increase, so the upper value can be adjusted based on patient feedback either during clinical trials or during patient treatment. According to various implementations, this desired integrated electric charge is generated when the applicator surface is positioned between, for example, 0 mm and 10 mm above and substantially parallel to the skin layer of the patient (see FIG. 3A).

While pulse generating circuit 131 is shown in FIG. 1A as part of base unit 120, pulse generating circuit 131 may be incorporated in applicator 150, for example, in close proximity to coil 166, and driven by signals generated by processor 122 from base unit 120. Pulse generating circuit 131 may include one or more capacitors with a rated voltage of approximately 1300-1700 volts and a rated capacitance of approximately 70-110 microfarads, e.g., 90 microfarads in one example. In some implementations, pulse generating circuit 131 may be specified to recapture at least 75% of the electrical energy from the capacitors. The charging and discharging of the capacitors generates a pulsed waveform through the coil that approximates a desired function in accordance with parameters 190. Other circuit elements may also be included to shape the pulsed waveform, such as polarity switchers and variable resistors. The particular pulsed waveform generated by way of a given set of parameters is used to energize coil 166 in a corresponding manner, which in turn generates a corresponding magnetic field that induces an effective amount of electrical current in the muscle tissues of patient 112.

Applicator 150 includes a housing 164 and a handle 160 for holding by an operator, such as operator 110. Housing 164 contains coil 166 in a fixed position with an axis of coil 166 substantially perpendicular to an applicator surface of the housing and may be formed from a molded plastic or other material. Housing 164 may preferably be a material with low thermal conductivity to prevent skin burns and improve comfort. Coil 166 may be a high performance, tightly wound metallic coil, such as a copper coil. In some implementations, the outer diameter of coil 166 may be approximately 130 mm, the inner diameter of coil 166 may be approximately 30 mm, and the winding cross sections of coil 166 may be approximately 7 mm to 8 mm by 1.8 mm. The windings of coil 166 may be formed from a single or multistranded wire. In some implementations, approximately 24 windings may be provided in coil 166. The wire conductor may be coated with a non-conductive material. In some implementations, the windings of coil 166 may be litz-wire, in which each wire strand of a multistranded wire is separately insulated. According to various implementations, coil 166 may be configured as a planar coil. In some implementations, coil 166 may be a toroidal coil. According to various implementations, the (mean) azimuthal direction of current flow through the coil is substantially parallel to the applicator surface in contact or directly above the skin of the patient, with the axis of the coil substantially perpendicular to the applicator surface, such that the magnetic field flows through the skin into corresponding neuromuscular tissue of the patient. As depicted in FIG. 1A, coil 166 may be thermally coupled to cooling chamber 165, which may at least partially surround coil 166 and be at least partially filled with liquid coolant 142.

Since applicator 150 operates on electromagnetic principles, there is no need for electrode electrical contact with patient 112. In some implementations, an optional cover may be provided, which may serve as a removably attachable barrier to housing 164 to prevent contact between the applicator and the skin of patient 112 or clothing, and may further facilitate surface cooling, as coil 166 may elevate the temperature of housing 164. The presence of the cover provides a physical barrier that prevents contact of the applicator with the patient's skin or clothing. The barrier cover may be disposable and fabricated using materials with low thermal conductivity to increase comfort for patient 112. Alternatively or additionally, housing 164 may be shaped to help prevent contact (e.g., with the patient's skin or clothing), as described below in conjunction with FIG. 1C.

With a block diagram overview of system 100 now in place, it may be helpful to observe various perspective views of the components of system 100. FIG. 1B depicts perspective views of base unit 120 for use with system 100 of FIG. 1A, according to various aspects of the subject technology. As shown in FIG. 1B, base unit 120 may be coupled to casters for mobility. Human interface device 126 may be provided as a touchscreen display on top of base unit 120. Applicator 150 may be tethered to base unit 120 via a cable that provides current from power supply 130 and liquid coolant 142 from cooling system 140. As shown in FIG. 1B, applicator 150 may be conveniently docked to a side of base unit 120 via holder 128. While only a single applicator 150 is shown in the perspective views of FIG. 1B, implementations may include multiple applicators, which may be hardwired to or detachable from base unit 120. For example, dual applicators may be utilized, as shown in FIG. 1A.

Figure 1C:
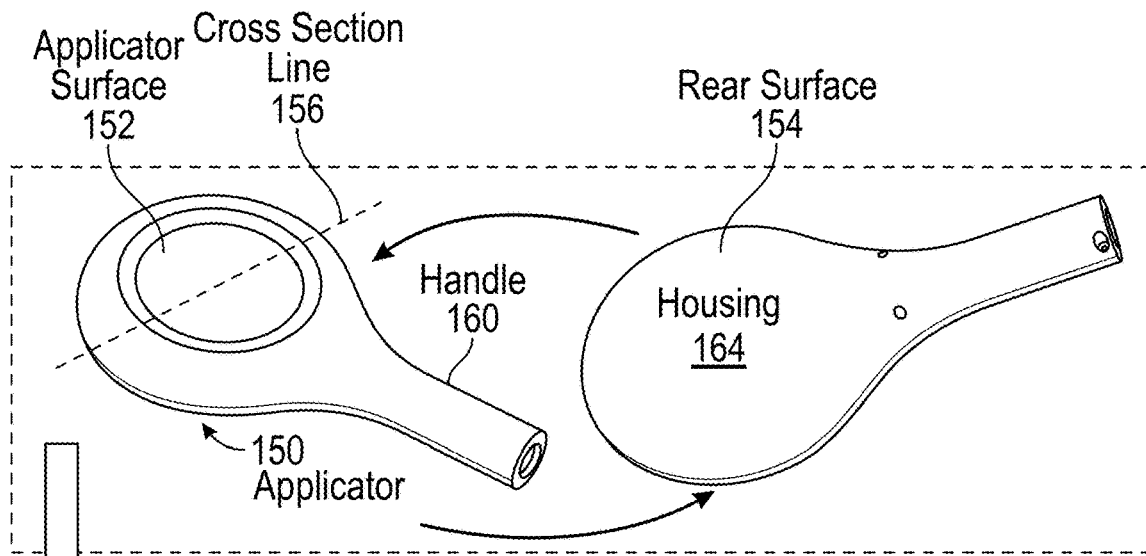
FIG. 1C depicts perspective views of an example electromagnetic applicator for use with the system of FIG. 1A, according to various aspects of the subject technology.
Figure 1D:
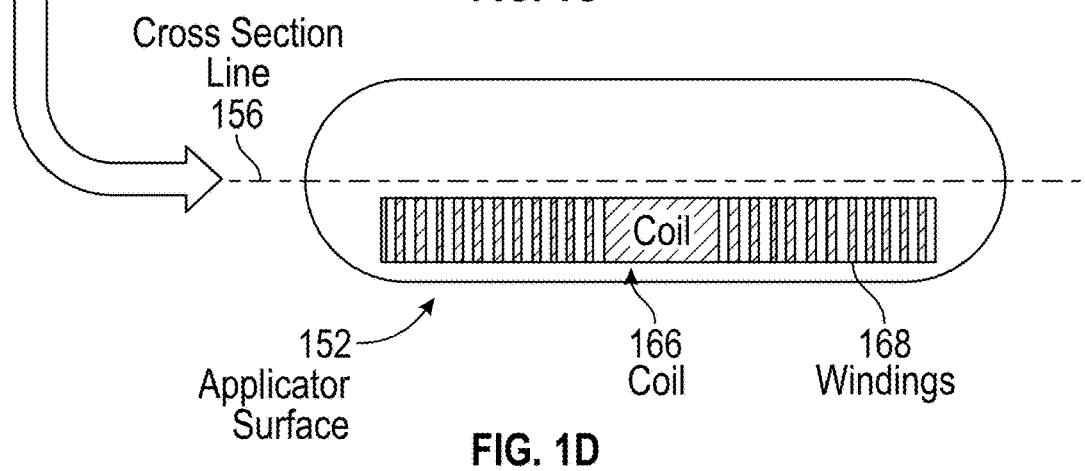
FIG. 1D depicts a cross-sectional view of the example electromagnetic applicator of FIG. 1C, according to various aspects of the subject technology.

FIG. 1C depicts perspective views of applicator 150 for use with system 100 of FIG. 1A, according to various aspects of the subject technology. As shown in FIG. 1C, housing 164 of applicator 150 may be a two-piece molded assembly that is fastened together, e.g., by screws, and includes applicator surface 152, rear surface 154, and handle 160. Of course, alternative implementations may use different materials, assembly techniques, and fasteners. Applicator surface 152 may be shaped as a substantially flat, circular surface to conform to the shape of coil 166. Applicator surface 152 may also be surrounded by raised edges of housing 164 to assist in preventing applicator surface 152 from contacting the skin of a patient. Alternatively or additionally, cover 164 (not shown) may be wrapped around housing 164.

FIG. 1D depicts a cross-sectional view of applicator 150 of FIG. 1C, according to various aspects of the subject technology. As shown in FIG. 1C and FIG. 1D, cross section line 156 cuts across the center of applicator 150 between applicator surface 152 and rear surface 154. Coil 166 includes windings 168 and is positioned close to applicator surface 152. While not specifically shown in FIG. 1D, applicator 150 may also include thermal interface materials to thermally couple coil 166 to pipes containing liquid coolant 142. For example, referring to FIG. 1A, applicator 150 may be provided with cooling chamber 165 that at least partially surrounds coil 166, wherein the cooling chamber is at least partially filled with liquid coolant 142. In this manner, the applicator surface 152 may be kept below an operating temperature of coil 166 when applicator 150 is in operation or receiving current from power supply 130.

FIG. 2A depicts example energy delivery values 290 of the system 100 of FIG. 1A, according to various aspects of the subject technology. FIG. 2A also depicts parameter range 292 and parameter set 294, also referred to as "operating parameters" that may be set to achieve one or more of energy delivery values 290. With respect to FIG. 2A, energy delivery values 290, parameter range 292, and/or parameter set 294 may correspond to parameters 190 from FIG. 1A.

Delivery values 290 have been found to bring about the optimal amount of neuro-stimulation in nerve fibers and neuromuscular tissue of a patient. It should be understood that example energy delivery values 290 can be programmed directly or generated by means of programing system 100 with a parameter set selected from operating parameters 292, 294. Delivery values 290, and/or operating parameters 292, 294, may be further adjusted according to individual use cases to balance, for example, electrical charge delivery to muscles, power consumption, thermal dissipation, and device form factor. When programmed directly (e.g., by way of user interface 126), system 100 may automatically calculate a parameter set 294 sufficient to achieve the desired delivery values 290.

A first value of delivery values 290, or tissue-independent integrated electrical charge/electrical conductivity ("delivery value") is defined to be at least 0.115 millivolt second meters (mV*s*m). In some implementations, the delivery value may be defined to exceed any of 0.12, 0.13, 0.14, 0.15, 0.16, 0.17, 0.18, 0.19, 0.20, 0.22, 0.25 mV*s*m, and be between 0.12-0.75 mV*s*m, and in one preferred embodiment exceeding 0.14 mV*s*m. In yet other implementations, the delivery value may be defined to be between 0.15 mV*s*m and 0.75 mV*s*m. These delivery values may be further calibrated to provide a desired level of muscle stimulation and patient discomfort. As described above, this delivery value is independent of variations in muscle response of individual patients.

Figure 2B:
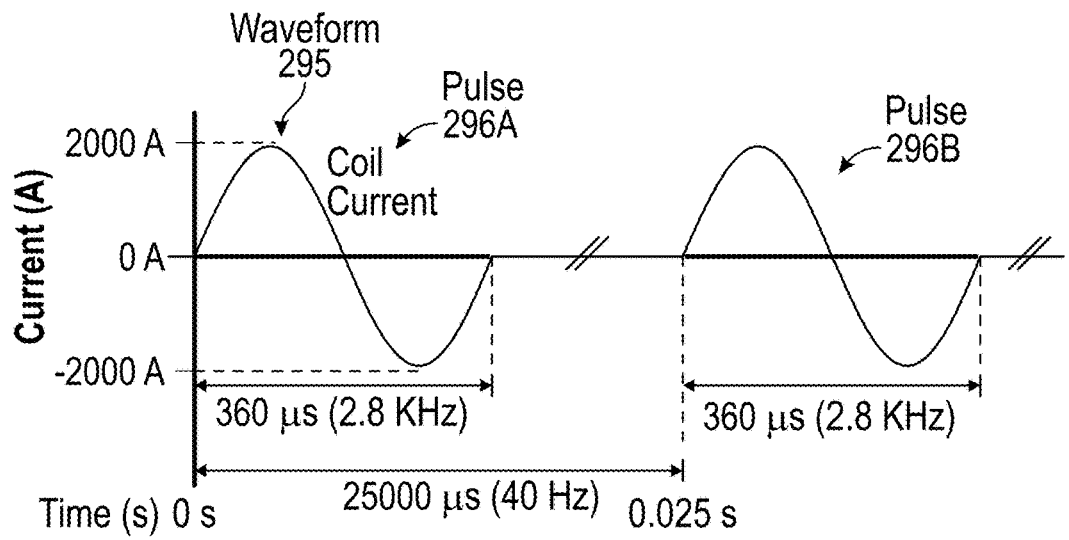
FIG. 2B depicts an example waveform to flow through coils of the electromagnetic applicator of FIG. 1C, according to various aspects of the subject technology.
Figure 2C:
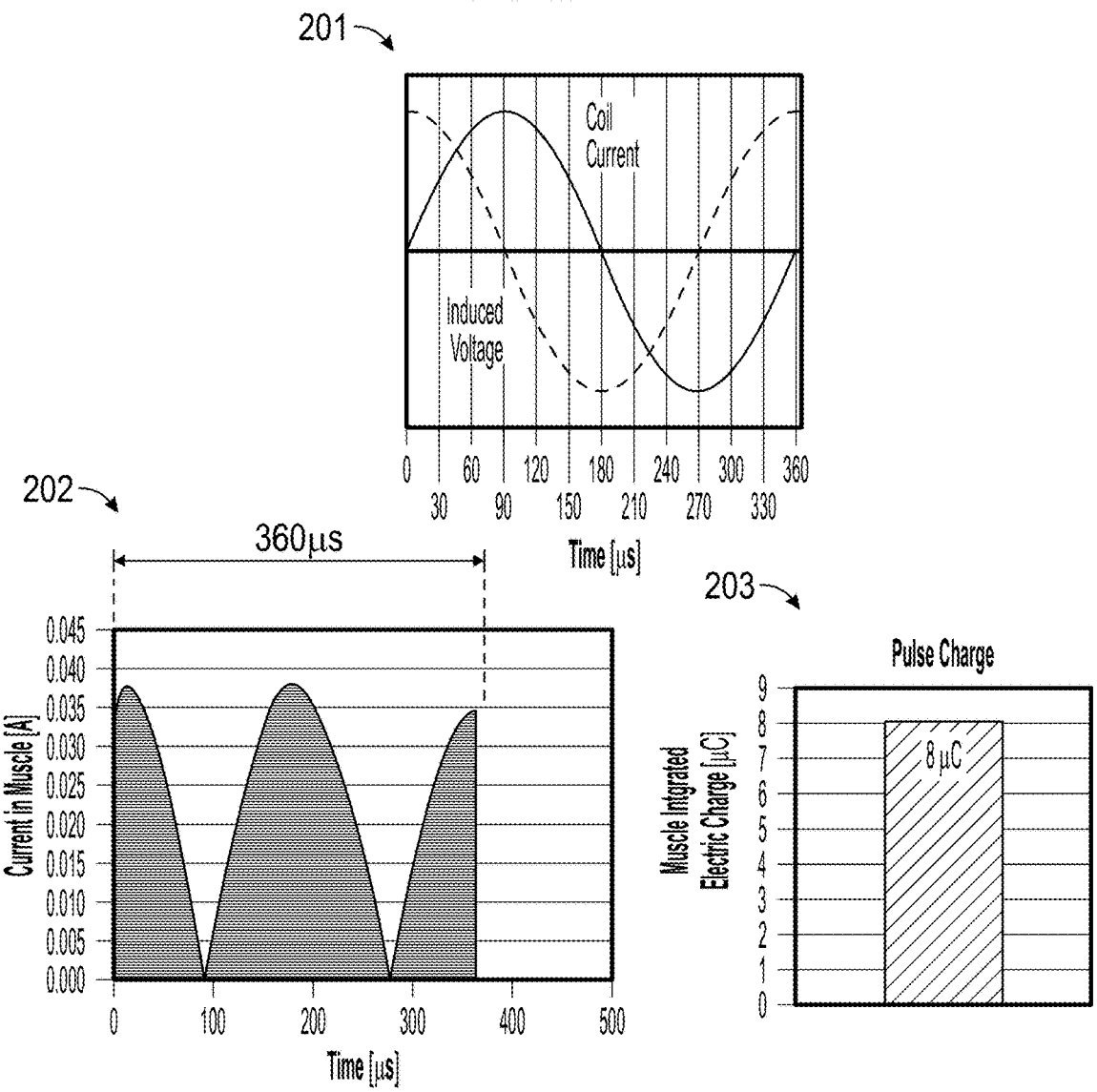
FIG. 2C depicts example measurements of current delivered to muscle tissues for a single pulse of the example waveform from FIG. 2B, according to various aspects of the subject technology.
Figure 2D:
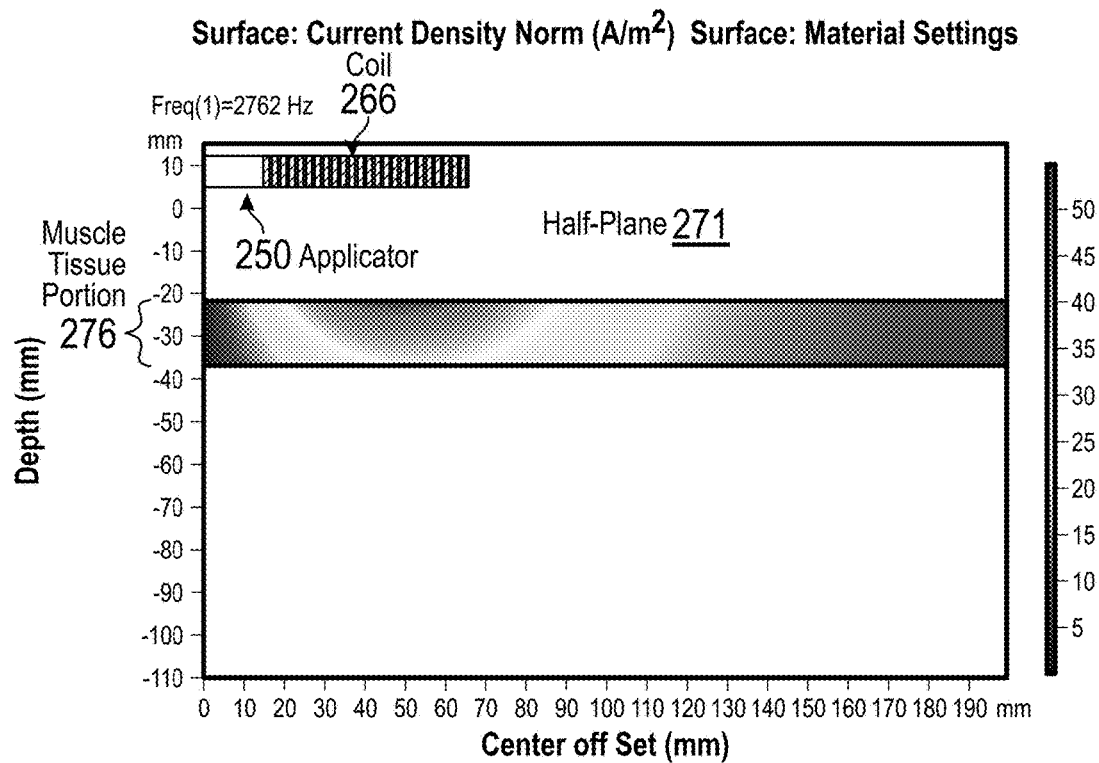
FIG. 2D depicts example measurements of current density norm in muscle tissues for a single pulse of the example waveform from FIG. 2B, according to various aspects of the subject technology.
Figure 2E:
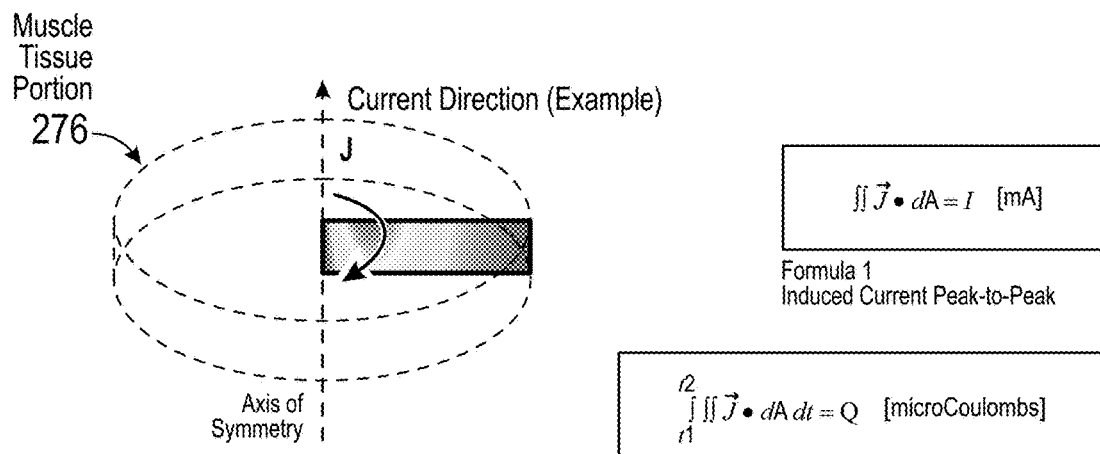
FIG. 2E depicts example calculations of induced current peak-to-peak and pulse charge for the example measurements of current density norm from FIG. 2D, according to various aspects of the subject technology.
Figure 2F:
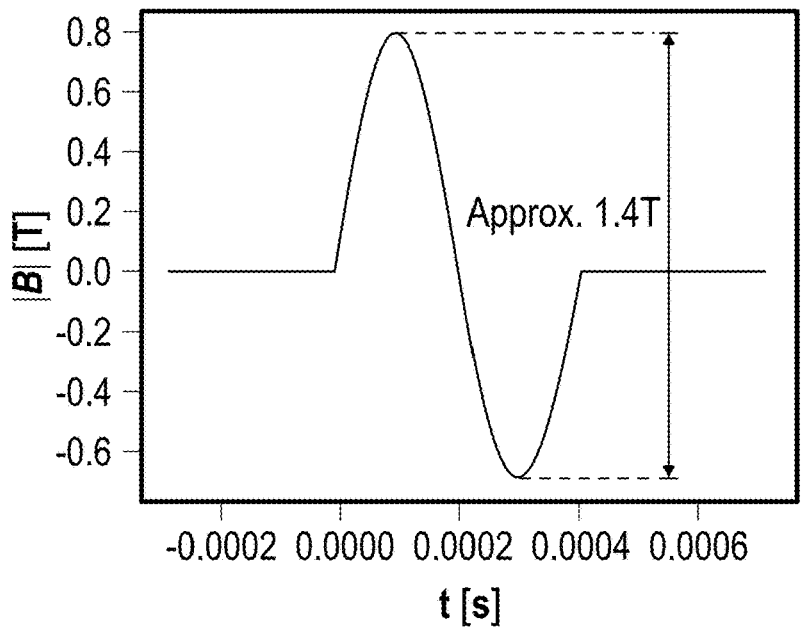
FIG. 2F depicts another example magnetic field waveform measurement resulting from a single pulse, according to various aspects of the subject technology, the pulsed waveform in FIG. 2F having a period of 400 microseconds, whereas the pulsed waveform in FIG. 2B has a period of 360 microseconds.
Figure 2G:
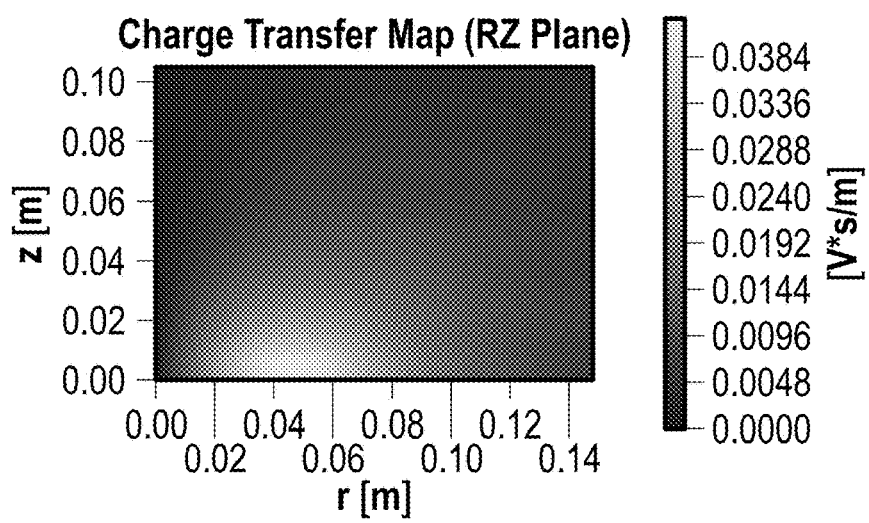
FIG. 2G depicts a charge transfer map resulting from a single pulse of the example waveform from FIG. 2F, according to various aspects of the subject technology.
Figure 2G:
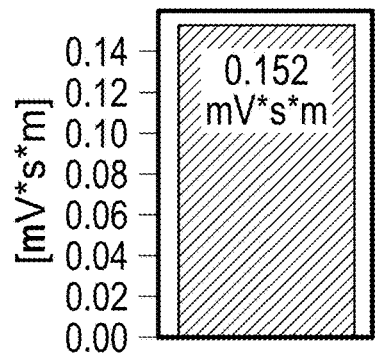

The delivery value may be defined with respect to an arbitrary portion or volume limit, for example by limiting charge measurements to a cylinder extending 0.10 m deep from applicator surface 152 with an axis corresponding to the axis of coil 166 and a radius of 0.15 m, as shown in FIG. 2G. Of course, the specific volume limit used may vary. One method of calculating a delivery value with a volume limit is described below in conjunction with FIG. 2G. Since the induced charge may rapidly decline in proportion to distance, charge outside the volume limit may be assumed to be negligible or close to zero, and thus imposing a volume limit may facilitate calculation of the delivery value while still providing a reasonably accurate estimate.

A second value of delivery values 290, or maximum magnetic flux density, is defined to be 1.3 to 1.4 Tesla (T). In alternative implementations, the maximum magnetic flux density may be defined to be 1.2 to 1.5 T, 1.1 to 1.6 T, or 1.0 to 2.0 T. This value may be measured from a vertical plane, labelled the "XZ" plane, which may be defined to be perpendicular to both applicator surface 152 and handle 160. For example, the magnetic field at several points within the XZ plane may be measured as a pulse flows through coil 166. The point exhibiting the highest measurements can then be used to determine the maximum magnetic flux density, as shown in FIG. 2F.

A third delivery value, or maximum current density norm, is defined to be at least 40 amps per square meter ($A/m^2$) and less than 100 $A/m^2$. An example measurement is illustrated below in conjunction with FIGS. 2D, 3A, and 3B.

A fourth delivery value, or induced current, peak-to-peak, is defined to be at least 70 milliamps (mA) and less than 200 mA. Example measurements are illustrated below in conjunction with FIG. 2E.

A parameter range 292 may be determined to generate delivery values 290, for example by experimental testing, model simulations, clinical testing, lookup tables, heuristics, or other methods. In some implementations, parameter range 292 may be a best effort range and not an exact match to satisfy delivery values 290. The parameter range 292 shown in FIG. 2A may satisfy the first parameter, or the delivery value being at least 0.115 mV*s*m. The ranges in parameter range 292 are defined for each pulse of current flowing through coil 166. In the examples illustrated in the Figures, the current flowing through coil 166 is specifically defined to be an AC pulsed waveform that is sinusoidal and biphasic, as shown in FIG. 2B, and consists of a single 360-degree pulse for each muscle stimulation period (e.g., if the muscle stimulation frequency is 50 Hz, one 360-degree pulse is delivered 50 times a second). The treatment waveform may include a series of pulses, which cycle between high and low frequency portions, to cause polyphasic muscle stimulation in a patient, and more particularly triphasic stimulation. However, other waveforms may also be used. The pulses, as shown in FIG. 2B may be by their nature, discontinuous, but the induced magnetic field is continuously time varying. At low stimulation frequency ranges of 0.5-10 Hz, 2-10 Hz, or preferably 3-10 Hz, used during the recovery period, the pulses are sufficiently spaced to allow the muscle to recover but still high enough to provide a continuously pulsed time-varying magnetic field in the patient's tissue.

Referring to FIG. 2A, a first parameter range 292 defines the pulse amplitude to be approximately 1500-2500 amps (A). A second parameter range 292 defines the pulse duration or width to be approximately 300-450 microseconds (μs), which corresponds to a frequency of approximately 2.2 to 3.3 kilohertz (KHz). A third parameter range 292 defines the pulse frequency to be 30 or more pulses per second (pps). When the waveform is specifically an AC waveform, the pulse frequency can also be defined in hertz (Hz). A fourth parameter range 292 defines the duty cycle to be 35% or greater. Here, the term duty cycle may refer to the percentage of time that the coil is intermittently excited by a high frequency waveform over time. For example, for a 35% duty cycle, the coil may repeatedly switch between two periods: one excitation period of 3.5 seconds, as shown in FIG. 2B, when the coil is intermittently excited by a pulsed waveform at a waveform frequency of 40 Hz, with each pulse having a duration of 360 microseconds and an individual pulse frequency of 2.8 kHz; and one recovery period (not shown in FIG. 2B) of 6.5 seconds when the coil is excited by a low frequency pulsed waveform, with each pulse having the same duration of 360 microseconds and an individual pulse frequency of 2.8 kHz. The waveform frequency may be, for example, 10-50 Hz. The individual pulse frequency may be, for example, 2.2-3.3 kHz. The duration of each pulse may be between 300-450 microseconds. The first period may be 2-12 seconds, and the second period may be 2-12 seconds. The low frequency portion of the waveform may have a waveform frequency of 0.5-10 Hz, for example, 1-10, 2-10, 3-10, 3-6, 4-8, 4-6, 5-7 or 4 to 5 Hz. Preferred duty cycles can be any duty cycle in excess of 35, 40, 45, 50, 55, 60, 65, 70, 75, 80, 85, 90, or 95%.

A combination of the first four parameter range 292, when combined with the electrical conductivity of the muscle being treated, defines a pulse charge per pulse, or integrated electric charge per pulse, of at least 6.4 micro-coulombs (μC). This defines a total amount of electric charge or electrons that the muscle tissues receive for each pulse, as shown in conjunction with FIG. 2C below.

As shown in parameter set 294, specific parameter values may be set within the ranges defined by parameter range 292. For example, pulse amplitude may be set to 2000 A, pulse duration or width may be set to 360 μs (approx. 2.8 KHz), waveform frequency may be set to 40 Hz, and duty cycle may be set to 50%. The resulting pulse charge may be measured to be 8 μC. In alternative implementations where waveforms other than sinusoidal biphasic AC are used, alternate waveform shapes and parameters may also be defined. The values in parameter set 294 may be predetermined and retrieved from non-volatile storage or may be calculated on the fly based on predetermined or adjustable delivery values 290. Optionally, parameter set 294 may be selected and/or adjusted based on input received from human interface device 126.

FIG. 2B depicts an example waveform 295 using parameter set 294 to flow through coil 166, according to various aspects of the subject technology. As shown in FIG. 2B, pulse 296A and pulse 296B both satisfy parameter set 294, which defines a pulse amplitude of 2000 A, a pulse width of 360 μs (2.8 KHz), and a waveform frequency of 40 Hz. Waveform 295 may continue repeating such that 40 pulses satisfying parameter set 294 are generated in one second, thereby satisfying the defined waveform frequency of 40 Hz. To satisfy the 50% duty cycle, alternating excitation and recovery periods of approximately equal time, such as 5 second excitation and 5 second recovery periods may be used, wherein waveform 295 having a higher waveform frequency (e.g., 40 Hz, 30-50 Hz) is output to the coil during the excitation periods, and a waveform having a lower waveform frequency (e.g., 0.5-10 Hz) is output to the coil during the recovery periods. It should be noted that FIG. 2B may not be drawn to scale to more clearly illustrate the waveform shapes of each pulse.

FIG. 2C depicts example measurements of current in muscle tissues for pulse 296A from FIG. 2B, according to various aspects of the subject technology. As shown in chart 201 of FIG. 2C, the coil current of pulse 296A generates an induced voltage (dotted line) into muscle tissue. The total current delivered to muscle tissues as a result of the induced voltage from pulse 296A is measured against time in chart 202. By calculating the area under the curve in chart 202, or the muscle integrated electric charge, a pulse charge of approximately 8 μC may be determined as shown in chart 203, which readily exceeds the minimum 6.4 μC pulse charge of parameter range 292 set forth in FIG. 2A. However, since the pulse charge may vary depending on individual muscle responses of different patients, it would be preferable to use a tissue-independent value to measure the efficacy of applicator 150 when using pulses defined by parameter set 294. A process for determining such a tissue-independent value is illustrated in conjunction with FIG. 2G below.

FIG. 2D depicts example measurements of current density norm in muscle tissue portion 276 for pulse 296A from FIG. 2B, according to various aspects of the subject technology. As shown in FIG. 2D and FIG. 2E, muscle tissue portion 276 is defined by a cylindrical cross section with a radius of approximately 200 mm at a depth of approximately 22 mm to 37 mm below a skin layer of a patient. Applicator 250 is placed such that the bottom surface of coil 266 is approximately 5 mm above and parallel to a skin surface layer of a patient, which may be assumed to be at depth 0 mm. Of course, the specific cross-sectional portion used for muscle tissue portion 276 may be arbitrarily defined to include the majority of electrical activity occurring in muscle tissue. Further, it should be understood that the depicted diagrams are idealized approximations, as the skin surface will not be perfectly flat in a real-world measurement.

When the windings 168 of coil 166 are precision constructed and tightly wound, the resulting magnetic field may be highly axisymmetric when coil 166 is energized. Thus, the magnetic field may be treated as axisymmetric to simplify calculations. The center offset may be defined relative to the axis of symmetry perpendicular to applicator surface 152, as shown in FIG. 2E. Thus, the left side edge of half-plane 271 is aligned with the center of coil 266. Due to the symmetry, only the positive plane, or half-plane 271, may be considered for integral calculations of muscle tissue portion 276.

Due to the inherent electrical properties of muscle tissue, muscle tissue more readily conducts induced electrical current from electromagnetic sources, such as coil 166 of applicator 150. Conversely, fat and nerve cells do not as readily conduct electrical current from electromagnetic sources (fat and nerve cells have higher electrical resistance), allowing applicator 150 to selectively target muscle tissue portion 276 with induced electrical currents and charge created by the changing magnetic and electrical fields. FIG. 2D shows the current density norm for muscle tissue portion 276 in an example patient according to induced current caused by pulse 296A flowing through coil 166. As shown in FIG. 2D, the portions closest to windings 168, or the portions near center offsets 20 mm to 80 mm, receive the highest current density norm, which may exceed 40 A/m$^2$ to satisfy the third value of delivery values 290. The highest current density norm may be less than 100 A/m$^2$.

FIG. 2E depicts example calculations of induced current peak-to-peak and pulse charge for the example measurements of current density norm from FIG. 2D, according to various aspects of the subject technology. As discussed above, since the magnetic field may be assumed to be axisymmetric, the formulas for determining the induced current peak-to-peak (Formula 1) and the pulse charge (Formula 2) can be simplified, as shown in FIG. 2E. By using Formula 1, the induced current peak-to-peak may be determined to be 70 milliamps (mA), satisfying the fourth value of delivery values 290. By using Formula 2, the pulse charge may be determined to be 8 µC, satisfying the range of at least 6.4 µC defined in parameter range 292 and consistent with the measurements shown in FIG. 2C.

FIG. 2F depicts an example magnetic field waveform measurement resulting from a pulse 296A having a period of 400 microseconds, according to various aspects of the subject technology. The magnetic field B may be measured against time at the XZ plane perpendicular to applicator surface 152 and handle 160. As shown in FIG. 2F, the maximum magnetic flux density is measured peak-to-peak to be approximately 1.4 T, satisfying the second value of delivery values 290.

FIG. 2G depicts a charge transfer map resulting from pulse 296A from FIG. 2F, according to various aspects of the subject technology. As discussed above, the magnetic field B can be assumed to be axisymmetric, in which case the XZ plane can also be interpreted to be the RZ plane, as the radius can be made equivalent to the X coordinate. To obtain the data points shown in FIG. 2G, several readings (e.g., 300 or more readings) may be taken across the RZ plane at depths 0 m to 0.10 m from applicator surface 152, as shown. Since the magnetic field B is assumed to be axisymmetric, only the positive half-plane may be considered in the charge transfer map, since the positive half-plane may be simply doubled to include the contribution of the negative half-plane. To calculate the total integrated charge/electrical conductivity from the charge transfer map, Faraday's law may be utilized, which may be expressed in integral form for axisymmetric systems:

Formula 3: Faraday's law in integral form for axisymmetric systems.

For a device using a 400-microsecond pulse (FIG. 2F), $|E_\theta(r)|$ may be integrated with respect to time to generate the charge transfer map shown in FIG. 2G, which measures the charge, or volt seconds per meter (V*s/m) along the RZ plane. To calculate the tissue-independent total integrated charge/electrical conductivity or the delivery value, the charge transfer map may be integrated with respect to the RZ half-plane, resulting in 0.152 mV*S*m for z depth 0 m to 0.10 m, radius r=0.15 m, as shown. This is consistent with the first value of delivery values 290, or a tissue-independent total integrated charge/electrical conductivity of at least 0.115 mV*s*m.

Figure 2H:
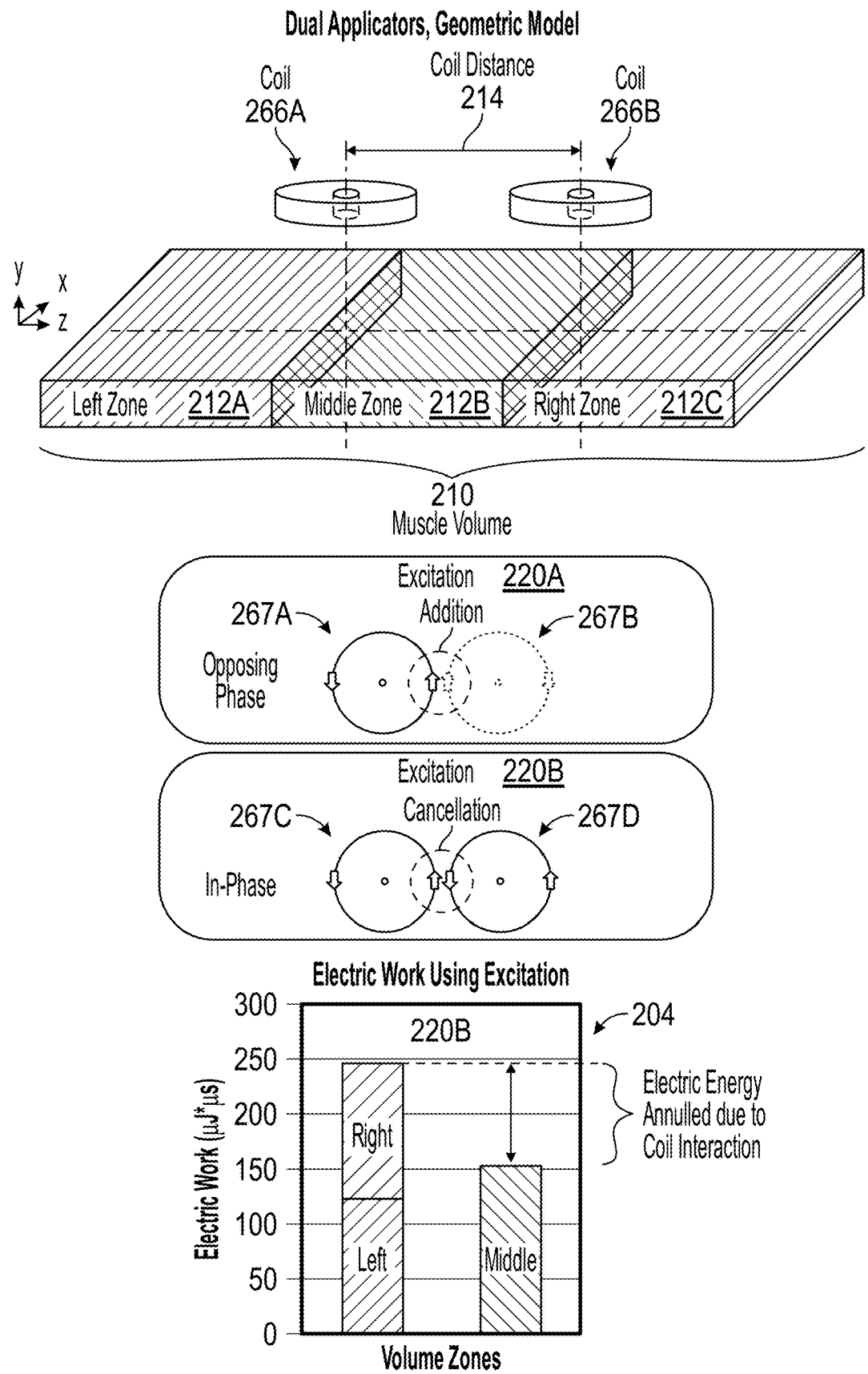
FIG. 2H depicts an example geometric model for dual applicators using phase adjusted coil excitation to deliver effective amounts of electromagnetic charge to muscle tissues, according to various aspects of the subject technology.

FIG. 2H depicts an example geometric model for dual applicators using phase adjusted coil excitation to deliver effective amounts of electromagnetic charge to muscle tissues, according to various aspects of the subject technology. Muscle volume 210 may correspond to a volume of muscle tissue at the same depth of muscle tissue portion 276 of FIG. 2D. For example, muscle volume 210 may be positioned at a depth approximately 22 to 37 mm below a skin surface of a patient, with a width (z axis) of approximately 510 mm, a length (x axis) of approximately 400 mm, and a height (y axis) of approximately 15 mm. Each zone, or left zone 212A, middle zone 212B, and right zone 212C may be of approximately equal size with a width of approximately 170 mm. Accordingly, coil distance 214 between the center of coil 266A and coil 266B may also be approximately 170 mm.

In some implementations, coil distance 214 may be maintained within a predetermined distance, such as 200 mm or less. In some implementations, the waveforms energizing coils 266A and 266B may be adjusted based on detecting the coil distance 214 between coils 266A and 266B. For example, when coil distance 214 is detected to pass below a predetermined low threshold or high threshold, then the phase offset of the waveforms energizing coils 266A and 266B may be adjusted. For example, the phase offset may decrease as coil distance 214 decreases, and vice versa.

The direction of the induced voltages may vary according to the current applied to coil 266A and 266B. For example, consider the example shown in excitation 220A, wherein the applied AC currents are opposing phases, e.g., having a phase offset of 180 degrees. When a positive current is applied to coil 266A, a magnetic field may extend above coil 266A, similar to magnetic field lines 380 shown in FIG. 3B, to result in a counterclockwise direction for induced voltage 267A. On the other hand, when a negative current is applied to coil 266B, a magnetic field may extend below coil 266B, resulting in a clockwise direction for induced voltage 267B. Note that the induced voltages 267A and 267B may therefore point in the same direction in an overlapping portion within middle zone 212B, causing the voltages to combine in an additive fashion. Thus, it can be observed that when the waveforms passed through coil 266A and 266B are in opposing phases, e.g., positive and negative, additive voltage interactions are incurred within middle zone 212B.

On the other hand, due to the attenuating effect of increasing distances, the effects of coil 266A on right zone 212C and coil 266B on left zone 212A may be considered to be minimal, and thus the induced voltages within left zone 212A can be largely attributed to coil 266A, and the induced voltages within right zone 212C can be largely attributed to coil 266B. Further, since the parameters of coil 266A and 266B may be similar with the possible exception of a phase offset, the induced voltage norm within left zone 212A may be substantially the same as within right zone 212C. Thus, to focus on the interactions between multiple coils in multiple applicators, only middle zone 212B may be considered, as left zone 212A and right zone 212C may be analyzed using the methods described above.

Consider now the example shown in excitation 220B, wherein the current applied to coil 266A and 266B are in-phase, or with a substantially zero phase offset. When a positive current is applied to both coil 266A and 266B, the resulting induced voltages 267C and 267D may both flow in the counterclockwise direction as shown. Within middle zone 212B, the induced voltages 267C and 267D may point in opposite directions, causing a cancellation of voltages. Thus, it can be observed that when the waveforms passed through coil 266A and 266B are in-phase, subtractive or cancellation voltage interactions are incurred within middle zone 212B.

Figure 2I:
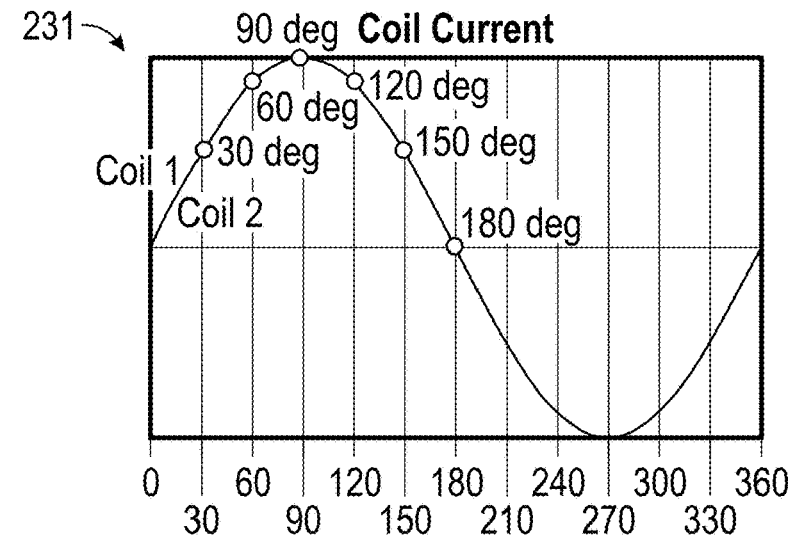
FIG. 2I depicts example graphs of coil current, induced voltage, and electric work for dual in-phase applicators using the geometric model of FIG. 2H, according to various aspects of the subject technology.
Figure 2I:
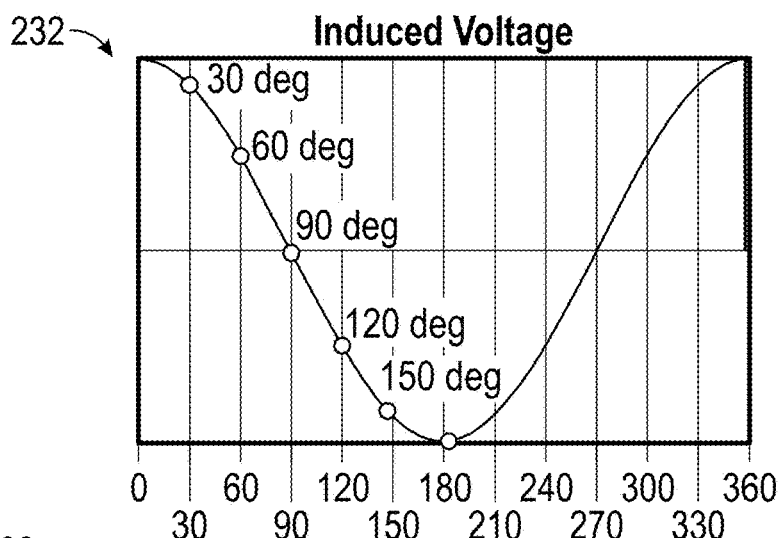
Figure 2I:
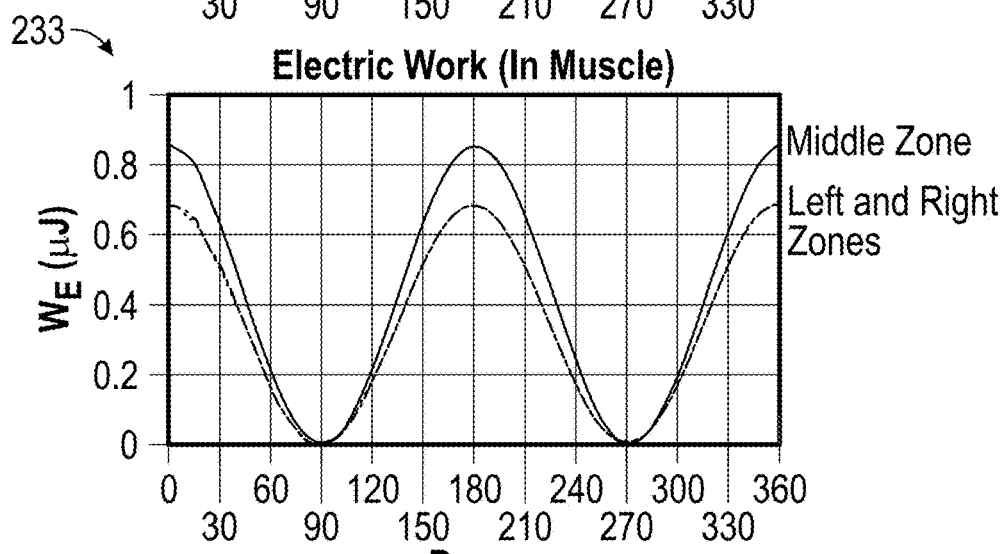

For example, chart 204 demonstrates the electric work induced in muscle volume 210 according to excitation 220B. As shown in chart 204, due to the cancellation effects of the in-phase excitation, the electric work provided in middle zone 212B is less than the combined electric work provided in left zone 212A and right zone 212C. To calculate the electric work in each target volume V or zones 212A-212C, the following formulas may be utilized:

FIG. 2I depicts example graph 231 of coil current, graph 232 of induced voltage, and graph 233 of electric work for dual in-phase applicators using the geometric model of FIG. 2H, according to various aspects of the subject technology. As shown in graph 231, both coil 266A ("Coil 1") and coil 266B ("Coil 2") have substantially the same waveform and are thus in-phase. Various phase offsets of the AC waveform are identified, including 30, 60, 90, 120, 150 and 180 degrees. Offsets from 180-360 degrees are not considered since the induced electrical field norm will be identical to 0-180 degrees.

As shown in graph 232, the maximum induced voltage is at 0 degrees and 180 degrees, whereas the minimum induced voltage is at 90 degrees and 270 degrees. This is consistent with graph 233, which shows the electrical work performed in muscle tissue in the three zones 212A-212C. To better visualize the results of graph 233, it may be helpful to view electric field norm readings at the identified phase offsets.

Figure 2J:
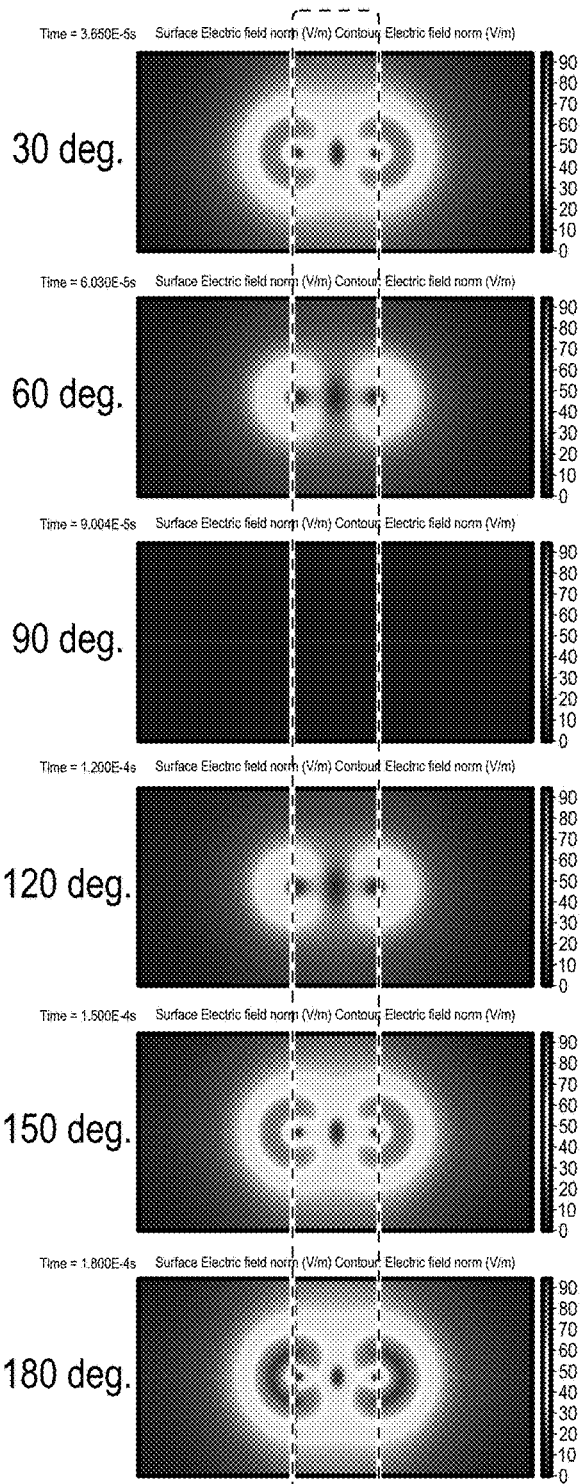
FIG. 2J depicts top and depth views of electrical field norm within muscle tissue layers when using dual in-phase applicators on the geometric model of FIG. 2H, according to various aspects of the subject technology.

FIG. 2J depicts top and depth views of electrical field norm within muscle tissue layers when using dual in-phase applicators on the geometric model of FIG. 2H, according to various aspects of the subject technology. The top view may be viewed at the depth of muscle tissue top layer 277, as identified by the dashed line in the depth view. Muscle tissue top layer 277 may be approximately 22 mm below the skin surface, as with muscle tissue portion 276 in FIG. 2D. As shown in the depth view, the electrical field norm within a middle portion of middle zone 212B is significantly reduced due to the cancellation occurring from the in-phase excitation. The same observation can be made from the depth view as well. Accordingly, excessively high electrical field can be advantageously avoided in middle zone 212B while still providing a large area of treatment for muscle stimulation.

Figure 2K:
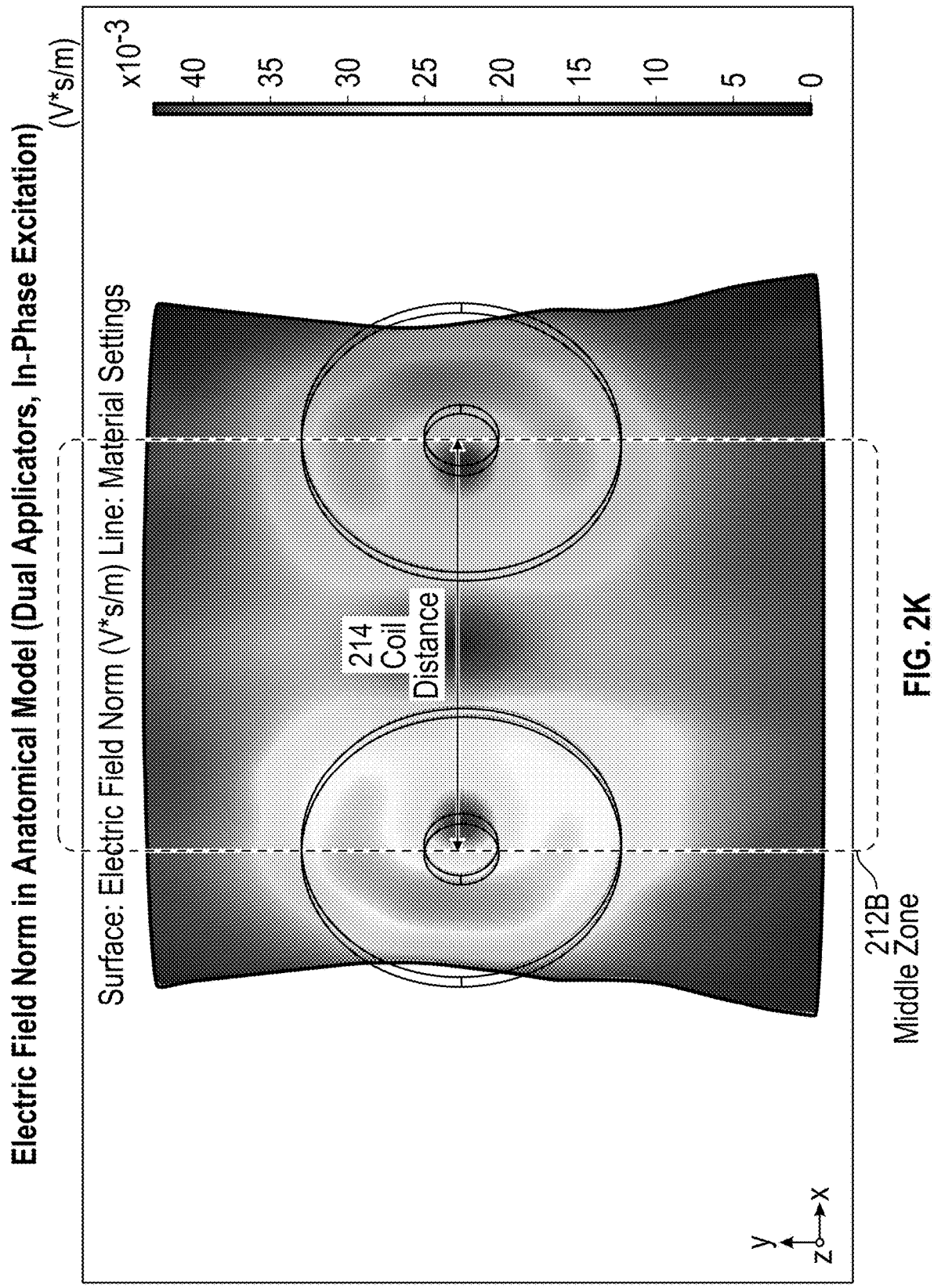
FIG. 2K depicts a top view of electrical field norm within muscle tissue layers when using dual in-phase applicators on an example anatomical model, according to various aspects of the subject technology.

FIG. 2K depicts a top view of electrical field norm within muscle tissue layers when using dual in-phase applicators on an example anatomical model, according to various aspects of the subject technology. As shown in FIG. 2K, when transitioning from an idealized geometric model to an anatomical model more closely following an actual human body, the results are largely the same—namely that the in-phase excitation of the dual applicators reduces the electric field norm within middle zone 212B. This enables the operator to safely maintain coil distance 214 within 200 mm or below to provide optimal stimulation coverage of the patient's body.

Figure 2L:
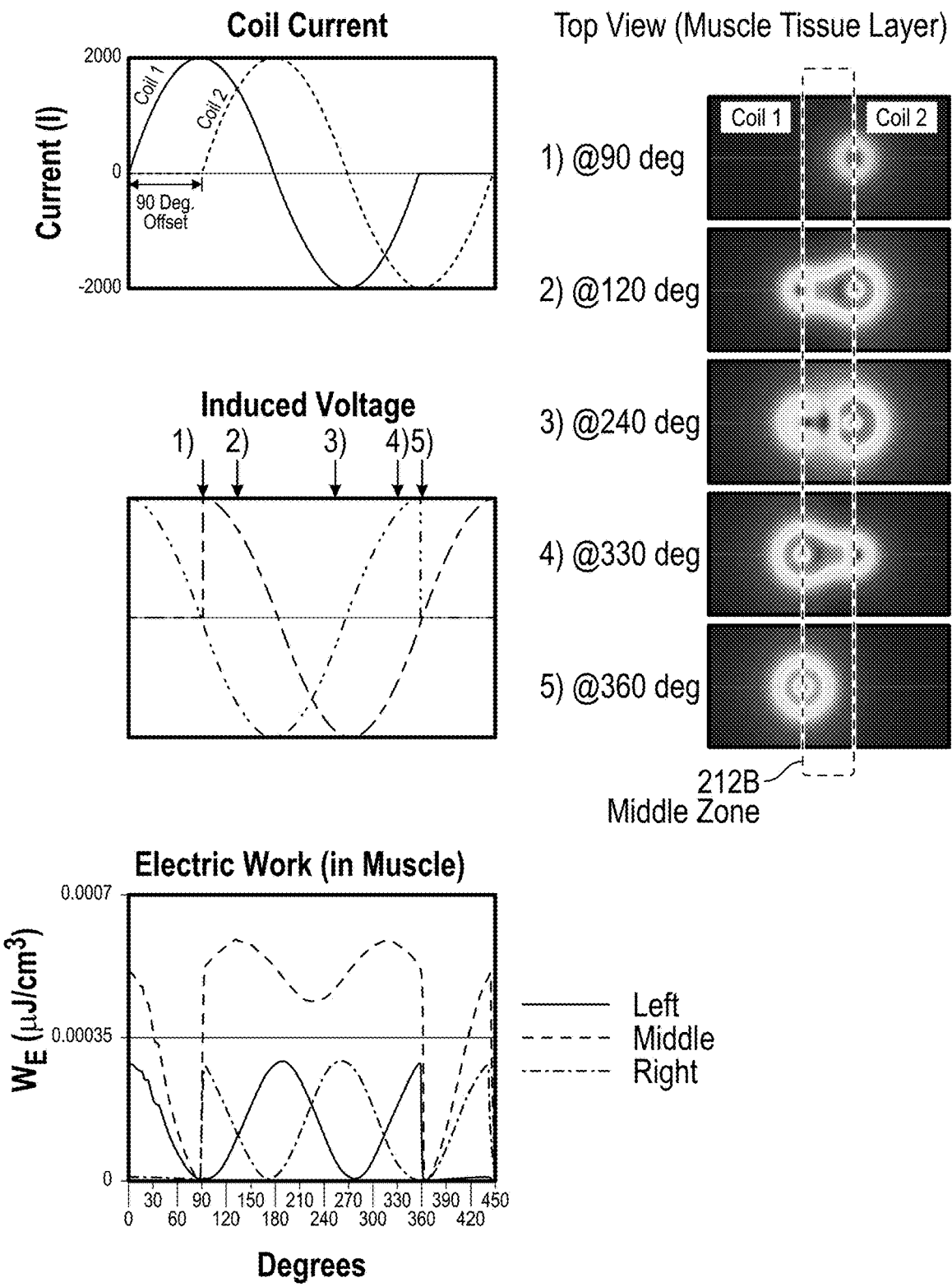
FIG. 2L depicts example graphs and top views of electrical field norm for dual applicators with a 90-degree phase offset on the geometric model of FIG. 2H, according to various aspects of the subject technology.

FIG. 2L depicts example graphs and top views of electrical field norm for dual applicators with a 90-degree phase offset on the geometric model of FIG. 2H, according to various aspects of the subject technology. As shown in the coil current graph, the AC waveform output to coil 1 and coil 2 are separated by a 90-degree phase offset. The resulting induced voltage and electric work graphs indicate that much less of the electric work is reduced as a result of the phase offset. This is clearly visible in the top view of the muscle tissue layer measured at 90, 120-, 240-, 330- and 360-degree offsets (identified as indexes 1, 2, 3, 4 and 5). For example, at indexes 2 and 5 or at 120- and 330-degree offsets, a substantial overlap of additive voltage can be seen within middle zone 212B, which may expose the patient to uncomfortable and possibly dangerous amounts of stimulation. Thus, it may be preferable to provide substantially in-phase coil excitation, for example by limiting the phase offset between coils to no greater than 90 degrees, no greater than 30 degrees, no greater than 10 degrees, no greater than 1 degree, or no greater than 0 degrees.

Figure 2M:
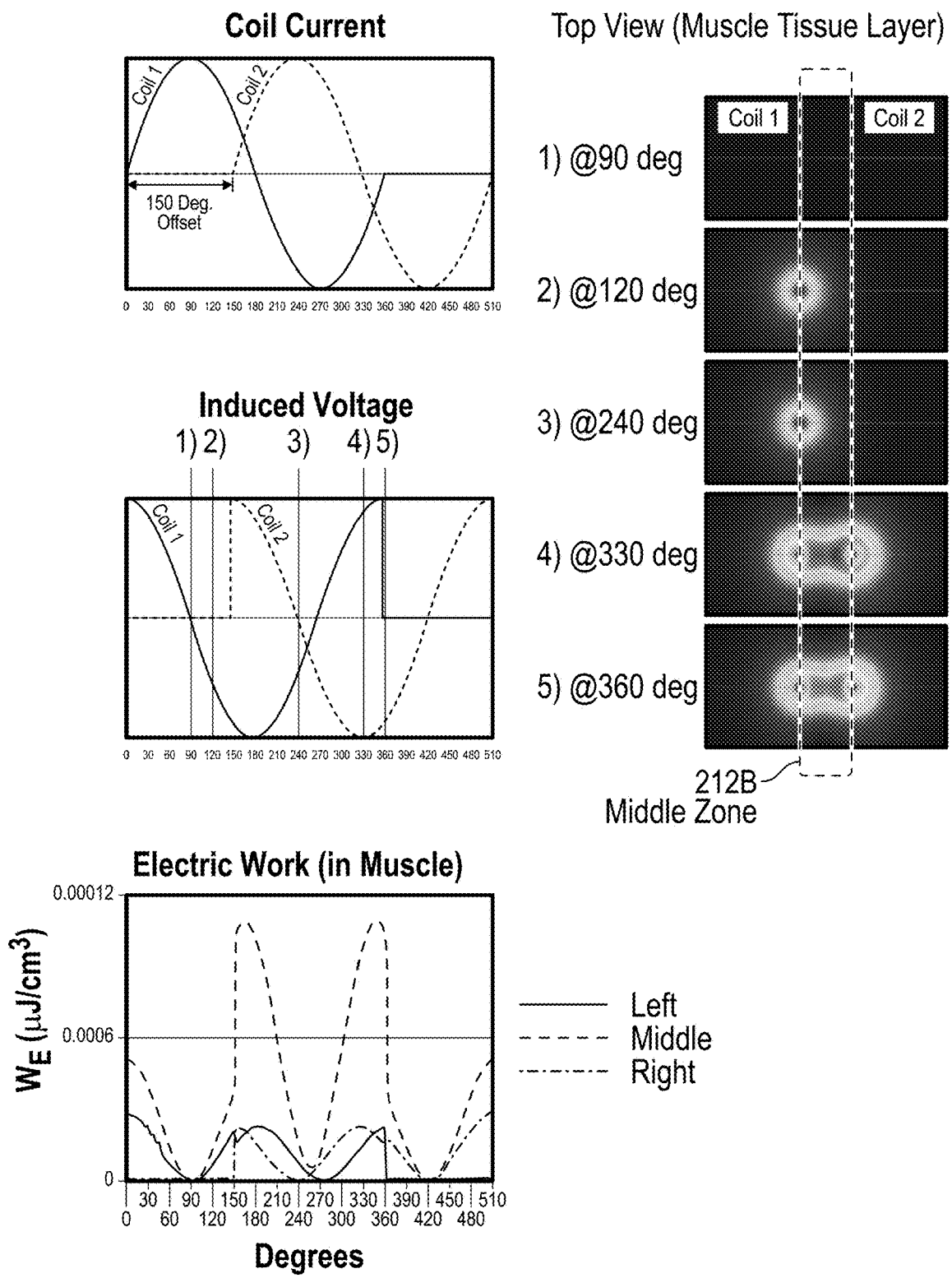
FIG. 2M depicts example graphs and top views of electrical field norm for dual applicators with a 150-degree phase offset on the geometric model of FIG. 2H, according to various aspects of the subject technology.

FIG. 2M depicts example graphs and top views of electrical field norm for dual applicators with a 150-degree phase offset on the geometric model of FIG. 2H, according to various aspects of the subject technology. Again, similar to FIG. 2L, the large phase offset of 150 degrees results in a significant overlap of additive voltage in middle zone 212B, as shown at indexes 4 and 5 or at 330- and 360-degree offsets.

Figure 3A:
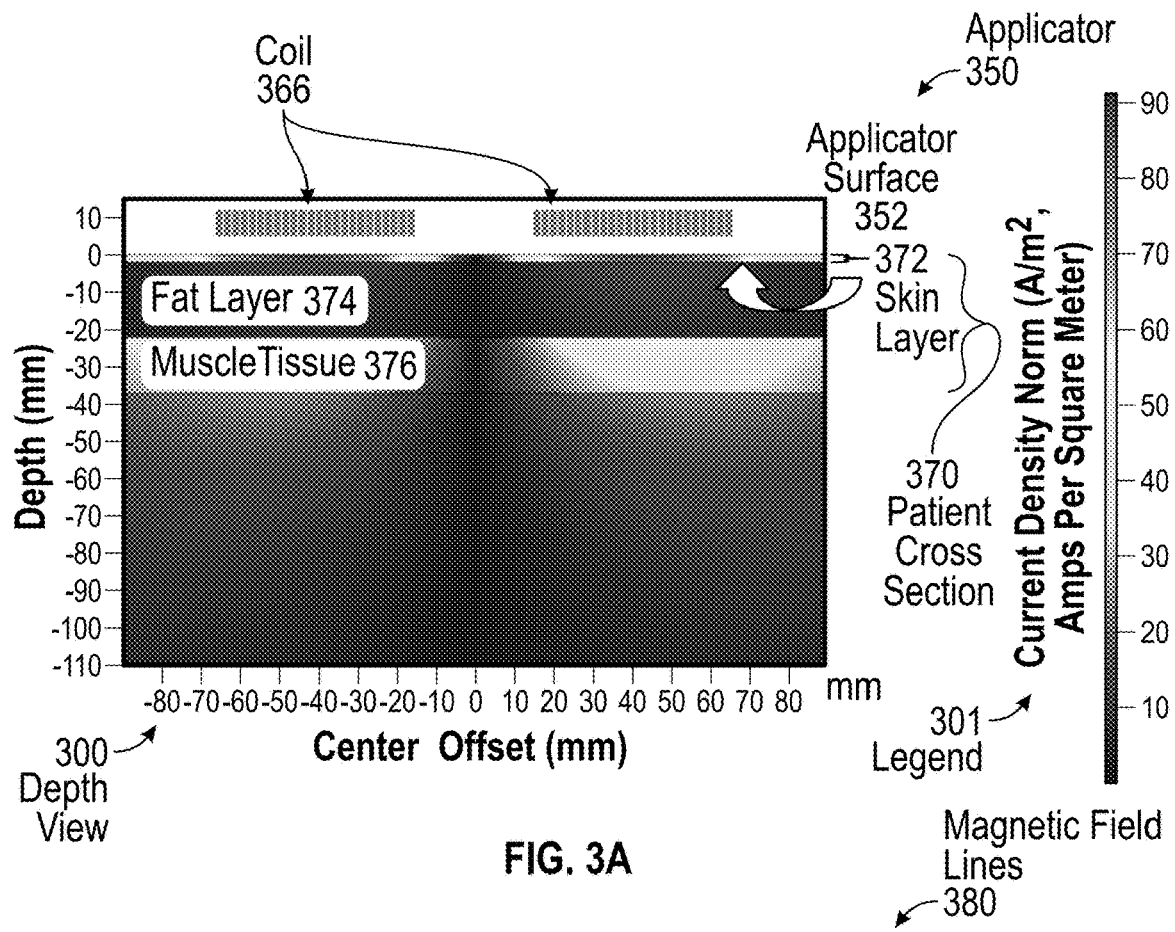
FIG. 3A and FIG. 3B respectively depict depth view and plane views of current density in a patient while using the electromagnetic applicator of FIG. 1C, according to various aspects of the subject technology.
Figure 3B:
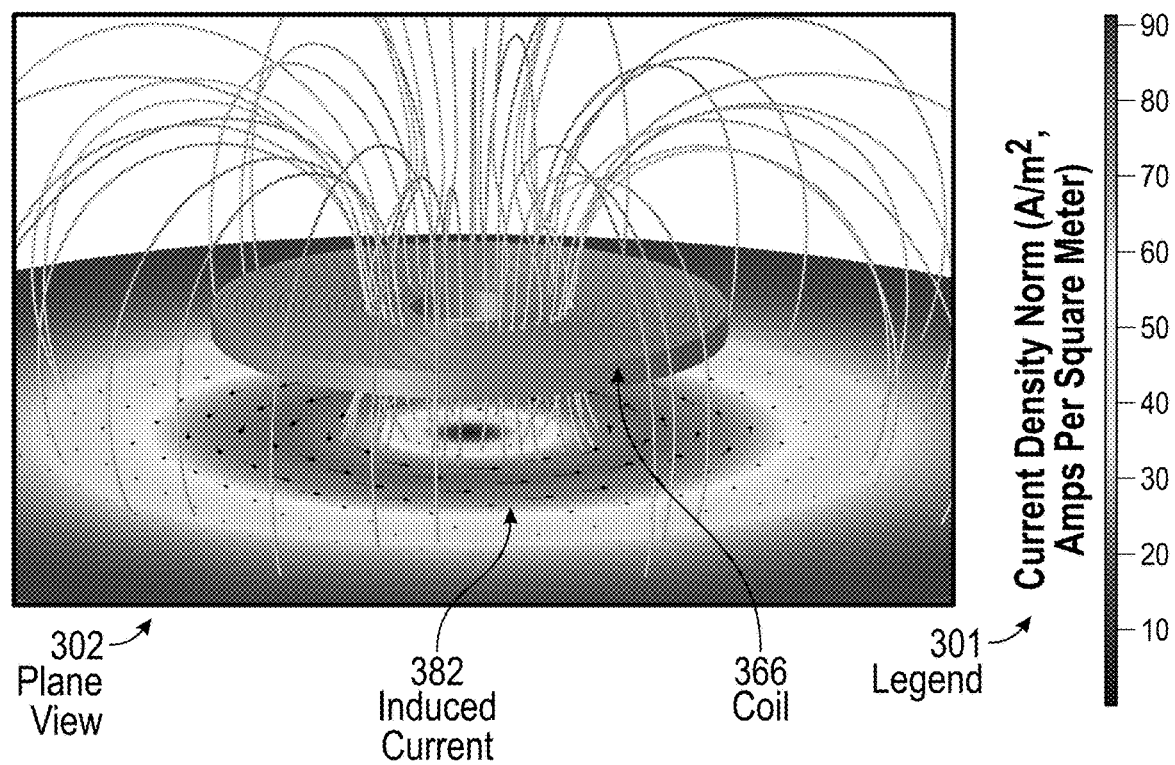

FIG. 3A and FIG. 3B respectively depict depth view 300 and plane view 302 of current density in an example patient while using applicator 350, according to various aspects of the subject technology. Applicator 350 includes coil 366 and applicator surface 352. FIG. 3A also includes legend 301 and patient cross section 370. Patient cross section 370 includes skin layer 372, fat layer 374, and muscle tissue 376. With respect to FIG. 3A and FIG. 3B, elements may correspond to like numbered elements from previous figures. For example, applicator 350 may correspond to applicator 150 from FIG. 1A-1D.

FIG. 3A may more clearly illustrate the selective application of current to muscle tissue 376. As shown in FIG. 3A, applicator 350 may be positioned such that applicator surface 352 is above and substantially parallel with skin layer 372. Coil 366 may be energized using parameter set 294 from FIG. 2A. As shown in depth view 300 and legend 301, due to the physical properties of fat layer 374 and muscle tissue 376, muscle tissue 376 may conduct current much more easily compared to fat layer 374, as indicated by the difference in current density.

Plane view 302 of FIG. 3B may correspond to a surface layer of skin layer 372. As shown in plane view 302, an axis of coil 366 may be substantially perpendicular to applicator surface 352. Magnetic field lines 380 are illustrated as being generated from coil 366. Of course, the individual field lines are only shown for exemplary purposes to illustrate the magnetic field. The magnetic field lines 380 cause a current to be induced in skin layer 372, as illustrated by induced current 382. A similar induced current is also generated in muscle tissue 376, but with reduced current density due to further distance from coil 366. As shown in FIG. 3B, the arrows indicate that induced current 382 is travelling counterclockwise in the instant captured by the figure. It will be appreciated that the induced current 382 oscillates between counterclockwise and clockwise as the coil is energized in an AC manner.

Figure 3C:
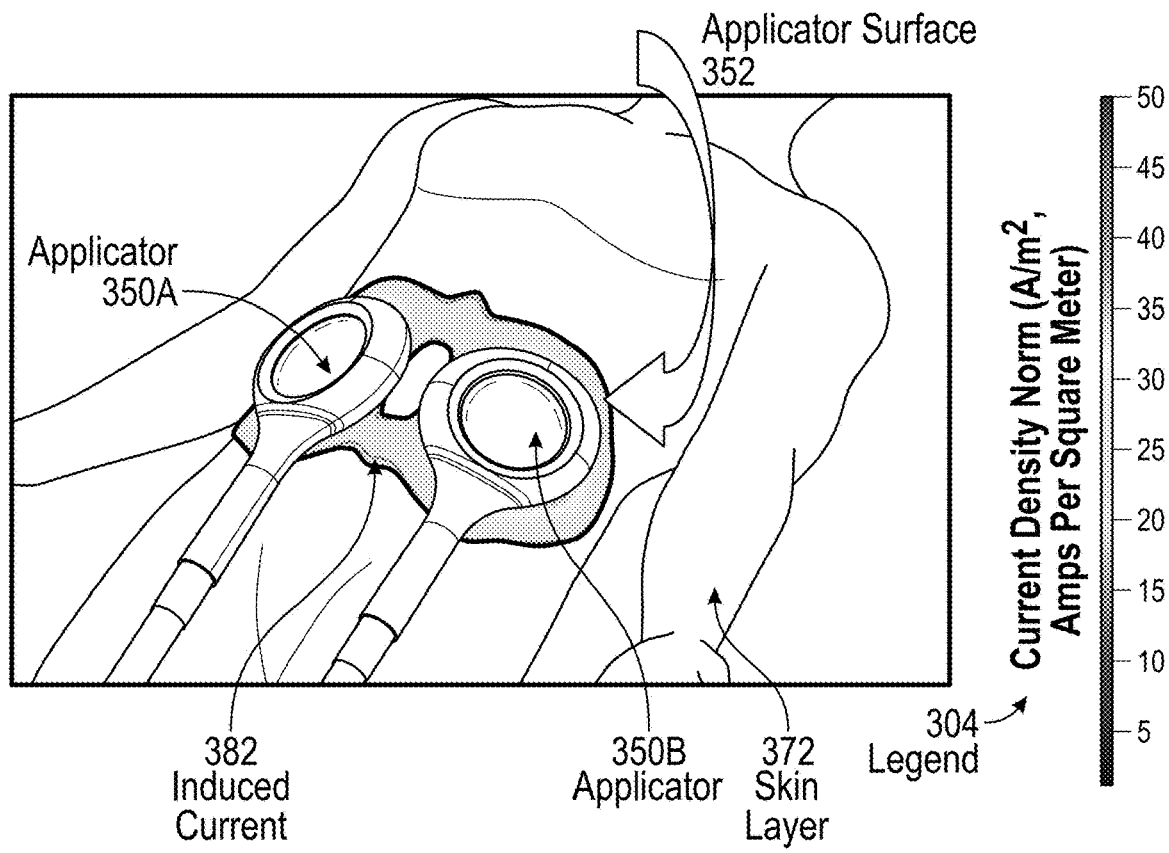
FIG. 3C and FIG. 3D depict overhead views of current density in a patient while using dual in-phase applicators, according to various aspects of the subject technology.
Figure 3D:
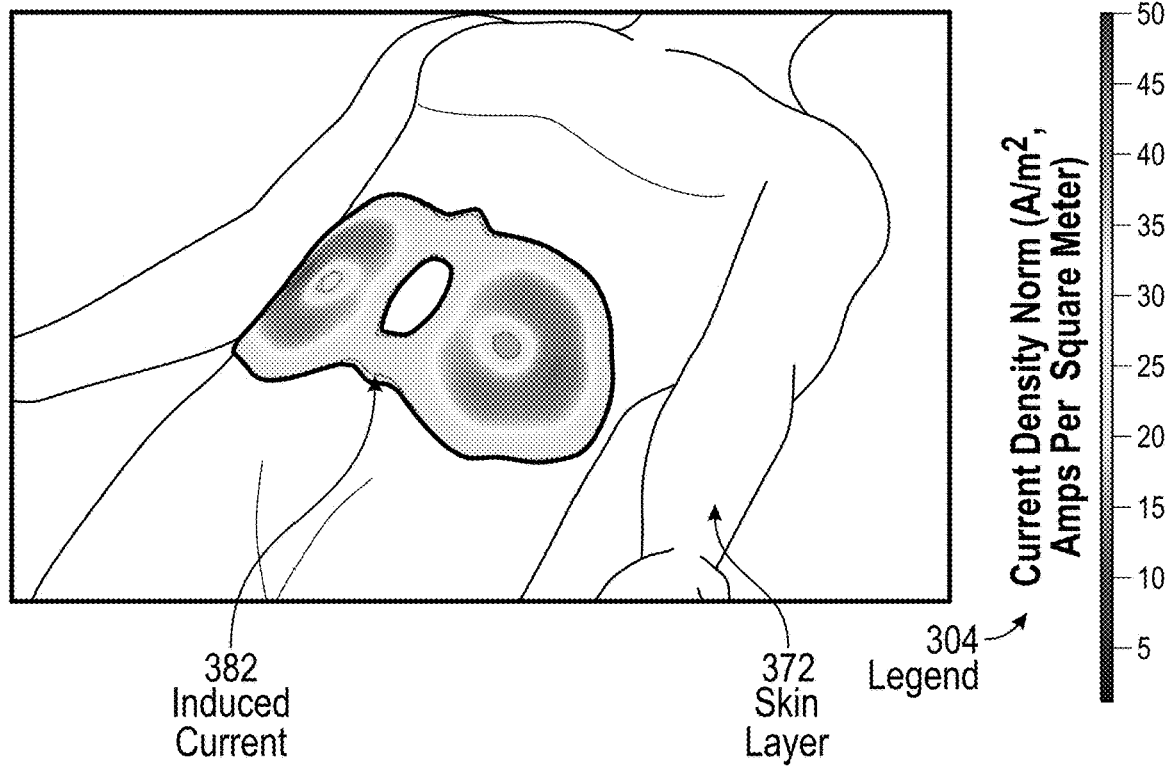

FIG. 3C and FIG. 3D depict overhead views of current density in a patient while using dual in-phase applicators, according to various aspects of the subject technology. As shown in FIG. 3C, applicator surface 352 of applicators 350A and 350B may be placed approximately parallel to the surface of skin layer 372, since skin layer 372 may not be uniformly flat due to individual body anatomy. To more clearly illustrate induced current 382, FIG. 3D omits applicators 350A and 350B. As shown in FIG. 3D, induced current 382 may have a maximum current density of approximately 45 A/m$^2$, satisfying the third value of delivery values 290.

Figure 4:
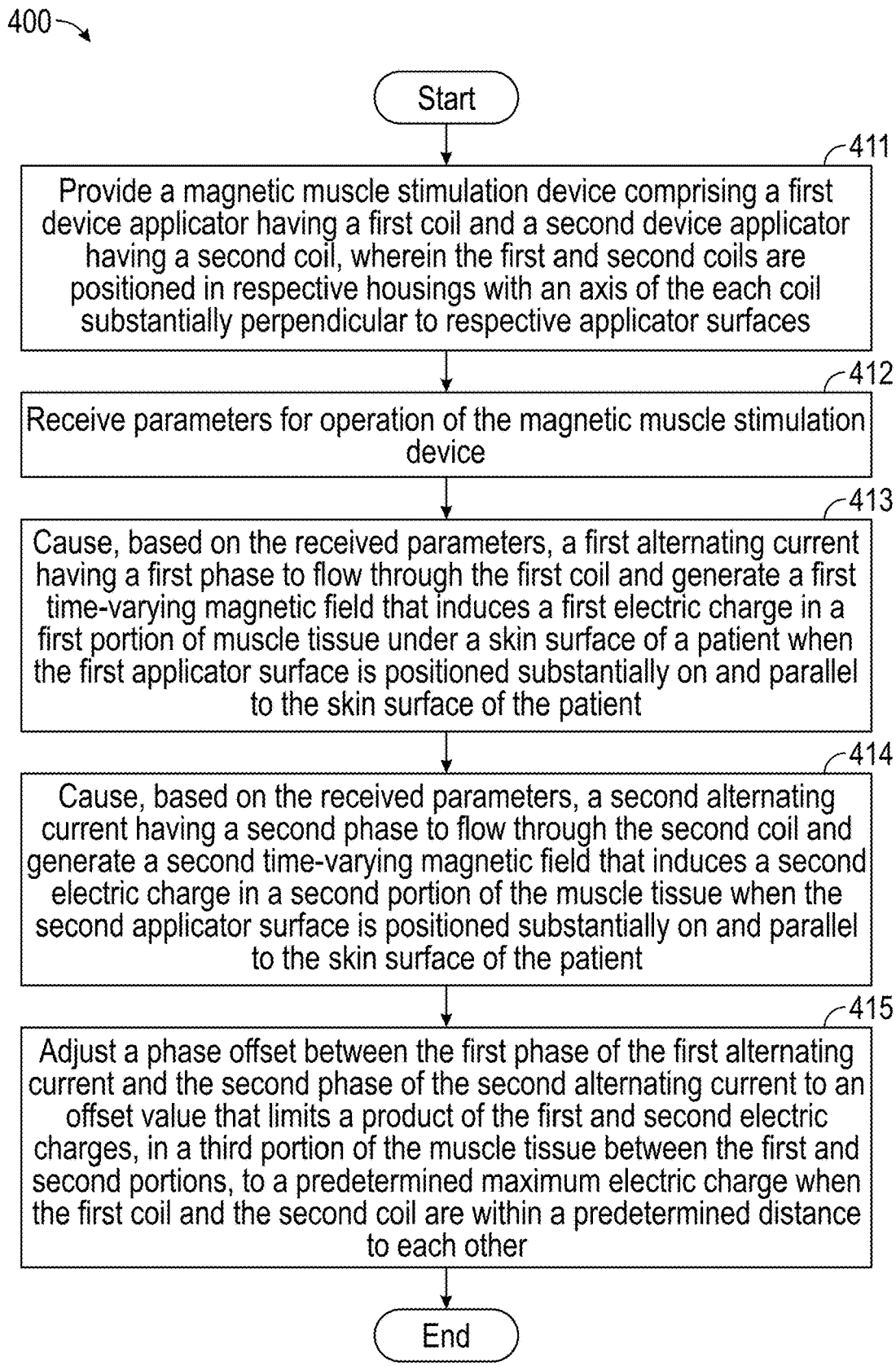
FIG. 4 depicts an example process for using phase adjusted coil excitation to deliver effective amounts of electromagnetic charge to muscle tissues, according to various aspects of the subject technology.

FIG. 4 depicts an example process 400 for using phase adjusted coil excitation to deliver effective amounts of electromagnetic charge to muscle tissues, according to various aspects of the subject technology. For explanatory purposes, the various blocks of example process 400 are described herein with reference to FIGS. 1A-3D, and the components and/or processes described herein. The one or more of the blocks of process 400 may be implemented, for example, by a computing device, including a processor and other components utilized by the device. In some implementations, one or more of the blocks may be implemented apart from other blocks, and by one or more different processors or devices. Further for explanatory purposes, the blocks of example process 400 are described as occurring in serial, or linearly. However, multiple blocks of example process 400 may occur in parallel. In addition, the blocks of example process 400 need not be performed in the order shown and/or one or more of the blocks of example process 400 need not be performed.

In the depicted example flow diagram, a magnetic muscle stimulation device is provided, comprising a first device applicator having a first coil and a second device applicator having a second coil, wherein the first and second coils are positioned in respective housings with an axis of each coil substantially perpendicular to respective applicator surfaces (411). Referring to FIG. 1A, this may correspond to providing base unit 120 with dual applicators 150. Referring to FIG. 1C and FIG. 1D, each applicator 150 has a coil 166 in housing 164. Referring to FIG. 3A and FIG. 3B, the applicator 350 corresponding to each applicator 150 has a coil 366 wherein an axis of coil 366 is substantially perpendicular to applicator surface 352.

Processor 122 may receive parameters 190 for operation of dual applicators 150 (412). As previously described, parameters 190 (FIG. 1A) may be predetermined or may be set according to user input received from human interface device 126. Using the example shown in FIG. 2A, parameters 190 in process 400 (FIG. 4) may correspond to satisfying the first value of delivery value 290, or providing a tissue-independent integrated electric charge/electrical conductivity of between 0.115 mV*s*m to 0.75 mV*s*m. In turn, a parameter range 292 may be determined to satisfy delivery values 290, and a specific parameter set 294 of parameter values may be determined to satisfy parameter range 292.

In some implementations, parameters 190 may specify a phase offset for excitation waveforms of the dual applicators, such as in-phase (0 degrees), or substantially in-phase (no greater than 1 degree, 10 degrees, 30 degrees, 90 degrees). Parameters 190 may also specify a maximum safe value of total tissue-independent integrated electric charge/electrical conductivity induced by all applicators. For example, a maximum safe value of 0.30 mV*s*m may be defined. To stay within the maximum safe value, the phase offset may be dynamically adjusted during excitation, e.g., during block 415 described below.

Processor 122 may continue to cause, based on the received parameters, a first alternating current having a first phase to flow through a first coil of a first applicator 150 to generate a time-varying magnetic field that induces a first electric charge in a first portion of muscle tissue under a skin surface of a patient when the applicator surface is positioned substantially on and parallel to the skin surface of the patient (413). Referring to FIG. 1A, FIG. 2F, FIG. 2G, FIG. 3A and FIG. 3C, this may correspond to processor 122 directing pulse generating circuit 131 of power supply 130 to output a waveform with a 400 μs period to flow through coil 366 of applicator 350 to generate a time-varying magnetic field illustrated by magnetic field lines 380 that induces a current, or induced current 382, having an integrated electrical charge, per pulse, of 0.152 mV*s*m in muscle tissue 376 under skin layer 372 when applicator surface 352 is positioned substantially on and parallel to skin layer 372 of patient 112. Referring to FIG. 2H, this may correspond to the above waveform being output to coil 266A, which induces a first electric charge in left zone 212A. As previously discussed, the measurement of the total integrated charge may be limited to an arbitrary region or volume limit to simplify calculations.

Processor 122 may continue to cause, based on the received parameters, a second alternating current having a second phase to flow through a second coil of a second applicator 150 to generate a time-varying magnetic field that induces a second electric charge in a second portion of muscle tissue under a skin surface of a patient when the applicator surface is positioned substantially on and parallel to the skin surface of the patient (414). Referring to FIG. 2H, this may correspond to the waveform from block 413 being output to coil 266B, which induces a second electric charge in right zone 212C. However, the waveform output to coil 266B may be phase delayed compared to the waveform output to coil 266A. Block 414 may thus proceed similarly as block 413, but with a potentially different second phase compared to the first phase.

Processor 122 may continue to adjust a phase offset between the first phase of the first alternating current and the second phase of the second alternating current to an offset value that limits a product of the first and second electric charges, in a third portion of the muscle tissue between the first and second portions, to a predetermined maximum electric charge when the first coil and the second coil are within a predetermined distance to each other (415). For example, referring to FIG. 2H, the phase offset between the first and second phases may be adjusted to an offset value to limit a product of the first and second electric charges in middle zone 212B. The offset value may be set to no greater than 90 degrees, 30 degrees, 10 degrees, 1 degree, or 0 degrees to limit the product of the first and second electric charges into middle zone 212B within a predetermined maximum electric charge when coil distance 214 is maintained within a predetermined distance, such as 200 mm or less.

For example, as discussed above, a maximum safe value of 0.30 mV*s*m may be defined. Based on the first and second electric charges within left zone 212A and right zone 212C, a maximum electric charge may be determined for middle zone 212B to keep a total electric charge within the maximum safe value. In some implementations, the predetermined maximum electric charge may be set for reasons of patient safety and comfort. In some implementations, the predetermined maximum electric charge may be set to maximize phase cancellation of the dual applicators. In some implementations, the phase may be dynamically adjusted by detecting coil distance 214. For example, the waveforms generated for the different coils may be adjusted during excitation to dynamically adjust the phase offset, for example adjusting towards in-phase excitation or smaller phase offset as coil distance 214 decreases and adjusting towards out-of-phase excitation or larger phase offset as coil distance 214 increases. Thus, the phase offset can also be adjusted upwards to increase the total electric charge for more effective muscle stimulation, for example when coil distance 214 is sufficiently large enough to prevent overstimulation.

The blocks of process 400 may be repeated if the parameters 190 are adjusted, for example by user input received from human interface device 126. Further, blocks 413-415 may continue for a predetermined period of time to perform a continuous stimulating of muscle tissue 376, which may be according to a duty cycle derived from parameter range 292.

Many aspects of the above-described example process 400, and related features and applications, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Figure 5:
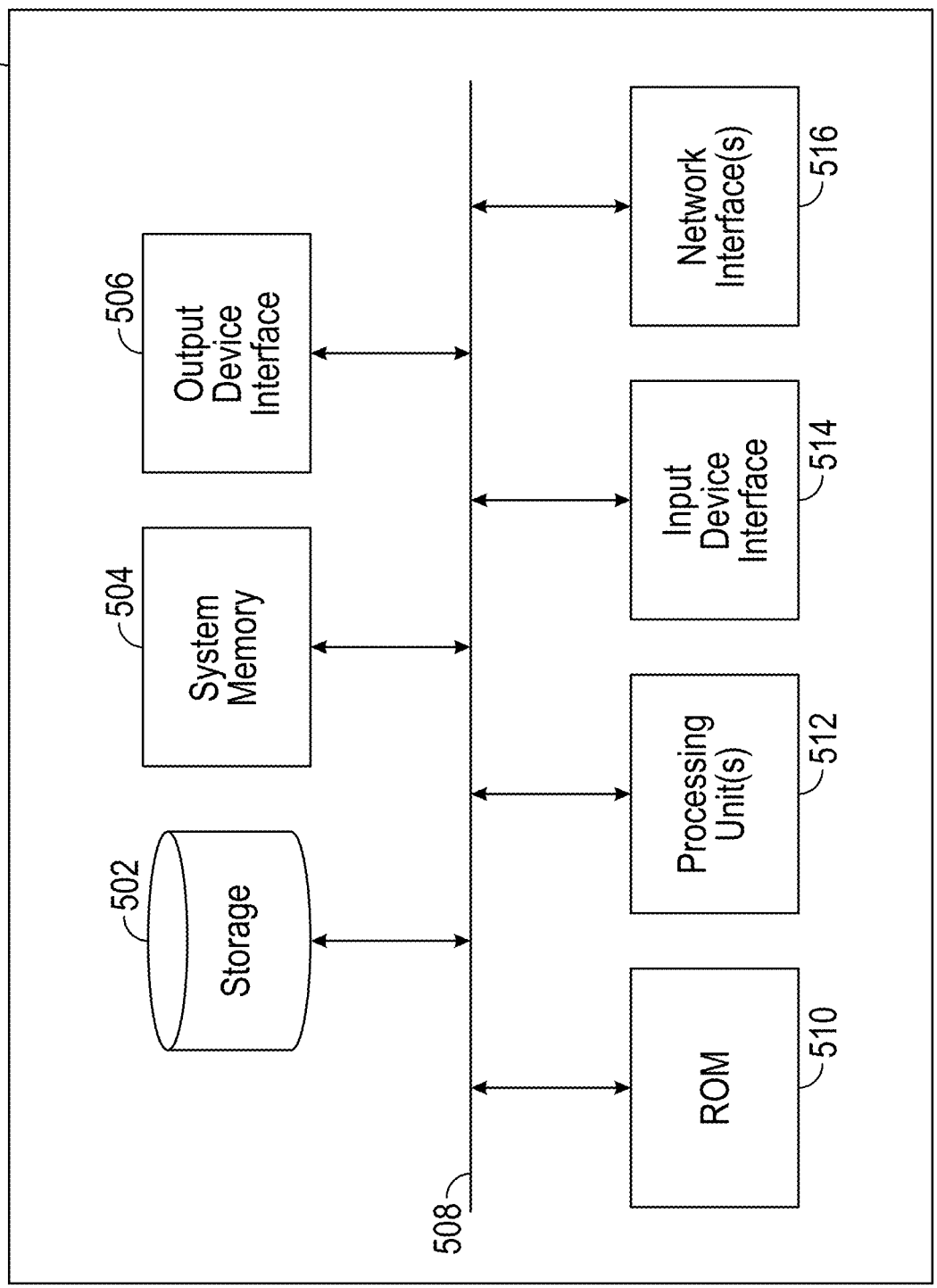
FIG. 5 is a conceptual diagram illustrating an example electronic system for using phase adjusted coil excitation to deliver effective amounts of electromagnetic charge to muscle tissues, according to various aspects of the subject technology.

FIG. 5 is a conceptual diagram illustrating an example electronic system 500 for using phase adjusted coil excitation to deliver effective amounts of electromagnetic charge to muscle tissues, according to various aspects of the subject technology. Electronic system 500 may be a computing device for execution of software associated with one or more portions or steps of process 400, or components and processes provided by FIGS. 1A-4. Electronic system 500 may be representative, in combination with the disclosure regarding FIGS. 1A-4, of the base unit 120 and/or the applicator 150 described above. In this regard, electronic system 500 may be a microcomputer, personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 500 may include various types of computer readable media and interfaces for various other types of computer readable media. In the depicted example, electronic system 500 includes a bus 508, processing unit(s) 512, a system memory 504, a read-only memory (ROM) 510, a permanent storage device 502, an input device interface 514, an output device interface 506, and one or more network interfaces 516. In some implementations, electronic system 500 may include or be integrated with other computing devices or circuitry for operation of the various components and processes previously described.

Bus 508 collectively represents all system, peripheral, and chipset buses that communicatively connect the numerous internal devices of electronic system 500. For instance, bus 508 communicatively connects processing unit(s) 512 with ROM 510, system memory 504, and permanent storage device 502.

From these various memory units, processing unit(s) 512 retrieves instructions to execute and data to process in order to execute the processes of the subject disclosure. The processing unit(s) can be a single processor or a multi-core processor in different implementations.

ROM 510 stores static data and instructions that are needed by processing unit(s) 512 and other modules of the electronic system. Permanent storage device 502, on the other hand, is a read-and-write memory device. This device is a non-volatile memory unit that stores instructions and data even when electronic system 500 is off. Some implementations of the subject disclosure use a mass-storage device (such as a magnetic or optical disk and its corresponding disk drive) as permanent storage device 502.

Other implementations use a removable storage device (such as a floppy disk, flash drive, and its corresponding disk drive) as permanent storage device 502. Like permanent storage device 502, system memory 504 is a read-and-write memory device. However, unlike storage device 502, system memory 504 is a volatile read-and-write memory, such a random-access memory. System memory 504 stores some of the instructions and data that the processor needs at runtime. In some implementations, the processes of the subject disclosure are stored in system memory 504, permanent storage device 502, and/or ROM 510. From these various memory units, processing unit(s) 512 retrieves instructions to execute and data to process in order to execute the processes of some implementations.

Bus 508 also connects to input and output device interfaces 514 and 506. Input device interface 514 enables the user to communicate information and select commands to the electronic system. Input devices used with input device interface 514 include, e.g., alphanumeric keyboards and pointing devices (also called "cursor control devices"). Output device interfaces 506 enables, e.g., the display of images generated by the electronic system 500. Output devices used with output device interface 506 include, e.g., printers and display devices, such as cathode ray tubes (CRT) or liquid crystal displays (LCD). Some implementations include devices such as a touchscreen that functions as both input and output devices.

Also, bus 508 also couples electronic system 500 to a network (not shown) through network interfaces 516. Network interfaces 516 may include, e.g., a wireless access point (e.g., Bluetooth or WiFi) or radio circuitry for connecting to a wireless access point. Network interfaces 516 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 500 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra-density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer," "server," "processor," and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit this disclosure.

The term website, as used herein, may include any aspect of a website, including one or more web pages, one or more servers used to host or store web related content, etc. Accordingly, the term website may be used interchangeably with the terms web page and server. The predicate words "configured to," "operable to," and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "implementation" does not imply that such implementation is essential to the subject technology or that such implementation applies to all configurations of the subject technology. A disclosure relating to an implementation may apply to all implementations, or one or more implementations. An implementation may provide one or more examples. A phrase such as an "implementation" may refer to one or more implementations and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A magnetic muscle stimulation device for strengthening, toning, and firming muscle tissues, the magnetic muscle stimulation device comprising:

a first device applicator comprising a first housing having a substantially flat first applicator surface, and a first coil positioned in the first housing with an axis of the first coil substantially perpendicular to the first applicator surface;

a second device applicator comprising a second housing having a substantially flat second applicator surface, and a second coil positioned in the second housing with an axis of the second coil substantially perpendicular to the second applicator surface; and a processor configured to:
  receive parameters for operation of the first and second device applicators;
  cause, based on the received parameters, a first alternating current having a first phase to flow through the first coil and generate a first time-varying magnetic field that induces a first electric charge in a first portion of muscle tissue under a skin surface of a patient when the first applicator surface is positioned on and parallel to the skin surface of the patient;
  cause, based on the received parameters, a second alternating current having a second phase to flow through the second coil and generate a second time-varying magnetic field that induces a second electric charge in a second portion of the muscle tissue when the second applicator surface is positioned on and parallel to the skin surface of the patient; and
  adjust a phase offset between the first phase of the first alternating current and the second phase of the second alternating current to a first offset value that limits a product of the first and second electric charges, in a third portion of the muscle tissue between the first and second portions, to a first predetermined maximum electric charge when the first coil and the second coil are within a first predetermined distance to each other.

2. The magnetic muscle stimulation device of claim 1, wherein the phase offset is no greater than 30 degrees.

3. The magnetic muscle stimulation device of claim 1, wherein the phase offset is no greater than 10 degrees.

4. The magnetic muscle stimulation device of claim 1, wherein the phase offset is no greater than 1 degree.

5. The magnetic muscle stimulation device of claim 1, wherein the processor is configured to receive the parameters specifying at least one of a biphasic, a triphasic, and a sinusoidal waveform to be used for the first or second alternating current.

6. The magnetic muscle stimulation device of claim 1, wherein the processor is configured to receive the parameters specifying a substantially identical waveform to be used for both the first and second alternating current.

7. The magnetic muscle stimulation device of claim 1, wherein causing the first and second alternating currents to flow through the first and second coils generates a combined time-varying magnetic field that induces a total integrated electric charge, per pulse, of between 0.115 millivolt second meters (mV*s*m) to 0.75 mV*s*m across a half plane of tissue having a side edge which is beneath a center of each of the first and second coils and which is about 140 mm wide and extending to about 100 mm below the skin surface of the patient when the first and second applicator surfaces are positioned within the predetermined distance of each other and on and parallel to the skin surface of the patient.

8. The magnetic muscle stimulation device of claim 1, wherein the first predetermined maximum electric charge is no greater than 0.30 millivolt second meters (mV*s*m).

9. The magnetic muscle stimulation device of claim 1, wherein the processor is configured to adjust the phase offset to maximize phase cancellation in the product of the first and second electric charges.

10. The magnetic muscle stimulation device of claim 1, wherein the processor is further configured to:
  detect a current distance between the first and second applicator surfaces; and
  adjust the phase offset according to the current distance between the first and second applicator surfaces.

11. The magnetic muscle stimulation device of claim 10, wherein adjusting the phase offset comprises reducing the phase offset when the current distance goes below a low threshold and increasing the phase offset when the current distance goes above a high threshold.

12. The magnetic muscle stimulation device of claim 1, wherein the first predetermined distance between the first and second applicator surfaces does not exceed 200 mm.

13. The magnetic muscle stimulation device of claim 1, wherein the phase offset is no greater than a threshold selected from the group consisting of 30 degrees, 10 degrees, 1 degree, and 0 degrees.

14. The magnetic muscle stimulation device of claim 1, wherein the processor is further configured to:
  adjust the phase offset between the first phase of the first alternating current and the second phase of the second alternating current to a second offset value.

15. The magnetic muscle stimulation device of claim 14, wherein the second offset value increases the product of the first and second electric charges, in the third portion of the muscle tissue between the first and second portions, to a second predetermined maximum electric charge when the first coil and the second coil are within a second predetermined distance to each other.

16. The magnetic muscle stimulation device of claim 14, wherein the phase offset is greater than 30 degrees.

17. The magnetic muscle stimulation device of claim 14, wherein the phase offset is no greater than 90 degrees.

18. The magnetic muscle stimulation device of claim 14, wherein the phase offset is no greater than 270 degrees.

19. The magnetic muscle stimulation device of claim 14, wherein the phase offset is no greater than 360 degrees.

20. The magnetic muscle stimulation device of claim 14, wherein the first predetermined distance is approximately the same as the second predetermined distance.

21. A method for strengthening, toning, and firming muscle tissues, the method comprising:
  providing a magnetic muscle stimulation device comprising a first device applicator having a first coil positioned in a first housing of the first device applicator, and a second device applicator having a second coil positioned in a second housing of the second device applicator, wherein the first and second housings have a substantially flat applicator surface, and wherein the first and second coils are positioned in the respective housings with an axis of each coil substantially perpendicular to the each respective applicator surface;
  receiving parameters for operation of the magnetic muscle stimulation device;
  causing, based on the received parameters, a first alternating current having a first phase to flow through the first coil and generate a first time-varying magnetic field that induces a first electric charge in a first portion of muscle tissue under a skin surface of a patient when the first applicator surface is positioned on and parallel to the skin surface of the patient;
  causing, based on the received parameters, a second alternating current having a second phase to flow through the second coil and generate a second time-varying magnetic field that induces a second electric charge in a second portion of the muscle tissue when the second applicator surface is positioned on and parallel to the skin surface of the patient; and
  adjusting a phase offset between the first phase of the first alternating current and the second phase of the second alternating current to an offset value that limits a product of the first and second electric charges, in a third portion of the muscle tissue between the first and second portions, to a predetermined maximum electric charge when the first coil and the second coil are within a predetermined distance to each other.

22. The method of claim 21, wherein the phase offset is no greater than 30 degrees.

23. The method of claim 21, wherein the phase offset is no greater than 1 degree.

24. The method of claim 21, further comprising:
  positioning the first applicator device and the second applicator device such that the first and second applicator surfaces are adjacent to each other and on and parallel to the skin surface of the patient, wherein the positioning causes the first and second alternating current to generate a combined time-varying magnetic field that induces a total integrated electric charge, per pulse, of between 0.115 millivolt second meters (mV*s*m) to 0.75 mV*s*m across a half plane of tissue having a side edge which is beneath a center of each of the first and second coils and which is about 140 mm wide and extending to about 100 mm below the skin surface of the patient.

25. The method of claim 21, wherein the predetermined maximum electric charge is no greater than 0.30 millivolt second meters (mV*s*m).

26. The method of claim 21, further comprising setting the phase offset to minimize phase cancellation in the product of the first and second electric charges.

27. The method of claim 21, further comprising:
  detecting a current distance between the first and second applicator surfaces; and
  adjusting the phase offset according to the current distance between the first and second applicator surfaces.

28. A non-transitory computer-readable medium comprising a plurality of instructions that, when read by a computing system, causes the computing system to perform a method of strengthening, toning, and firming muscle tissues, the method comprising:
  receiving parameters for operation of a magnetic muscle stimulation device comprising first and second device applicators, the first device applicator comprising a first housing having a substantially flat first applicator surface, and a first coil positioned in the first housing with an axis of the first coil substantially perpendicular to the first applicator surface; the second device applicator comprising a second housing having a substantially flat second applicator surface, and a second coil positioned in the second housing with an axis of the second coil substantially perpendicular to the second applicator surface;
  causing, based on the received parameters, a first alternating current having a first phase to flow through the first coil and generate a first time-varying magnetic field that induces a first electric charge in muscle tissue under a skin surface of a patient when the first applicator surface is positioned on and parallel to the skin surface of the patient;
  causing, based on the received parameters, a second alternating current having a second phase to flow through the second coil and generate a second time-varying magnetic field that induces a second electric charge in the muscle tissue when the second applicator surface is positioned on and parallel to the skin surface of the patient; and
  adjusting a phase offset between the first phase of the first alternating current and the second phase of the second alternating current to an offset value that limits a product of the first and second electric charges, in a third portion of the muscle tissue between the first and second portions, to a predetermined maximum electric charge when the first coil and the second coil are within a predetermined distance to each other.

* * * * *